(12) United States Patent
Surmeier, Jr. et al.

(10) Patent No.: US 10,105,366 B2
(45) Date of Patent: Oct. 23, 2018

(54) SELECTIVE CALCIUM CHANNEL ANTAGONISTS

(71) Applicant: Northwestern University, Evanston, IL (US)

(72) Inventors: Dalton J. Surmeier, Jr., Chicago, IL (US); Richard B. Silverman, Northbrook, IL (US); Soo Sung Kang, Wilmette, IL (US); Garry Cooper, Evanston, IL (US)

(73) Assignee: Northwestern University, Evanston, IL (US)

( * ) Notice: Subject to any disclaimer, the term of this patent is extended or adjusted under 35 U.S.C. 154(b) by 11 days.

(21) Appl. No.: 15/200,856

(22) Filed: Jul. 1, 2016

(65) Prior Publication Data
US 2016/0310491 A1 Oct. 27, 2016

Related U.S. Application Data

(63) Continuation of application No. 13/354,156, filed on Jan. 19, 2012, now Pat. No. 9,428,467.

(60) Provisional application No. 61/434,044, filed on Jan. 19, 2011.

(51) Int. Cl.
A61K 31/515 (2006.01)
C07D 239/62 (2006.01)

(52) U.S. Cl.
CPC .......... *A61K 31/515* (2013.01); *C07D 239/62* (2013.01)

(58) Field of Classification Search
CPC .......................... A61K 31/515; C07D 239/62
See application file for complete search history.

(56) References Cited

U.S. PATENT DOCUMENTS

| 2007/0049574 A1 | 3/2007 | Amrein et al. |
| 2012/0196883 A1 | 8/2012 | Surmeier, Jr. et al. |

FOREIGN PATENT DOCUMENTS

| WO | 2006/071730 | 7/2006 |
| WO | 2006/091544 | 8/2006 |
| WO | 2010/129665 | 11/2010 |

OTHER PUBLICATIONS

Morimoto, "Dynamic remodeling of transcription complexes by molecular chaperones," Cell 2002, 110(3),281-4.
Mosharov et al., "Interplay between cytosolic dopamine, calcium, and alpha-synuclein causes selective death of substantia nigra neurons," Neuron, 62: 218-229, 2009.
Nedergaard et al., "Nifedipine- and omega-conotoxin-sensitive Ca2+ conductances in guinea-pig substantia nigra pars compacta neurones," J Physiol, 466, 727-747, 1993.
Neumann et al., "Ubiquitinated TDP-43 in frontotemporal lobar degeneration and amyotrophic lateral sclerosis," Science, 2006, 314, 130-133.
Nollen et al., "Chaperoning signaling pathways: molecular chaperones as stress-sensing 'heat shock' proteins," J. Cell Sci. 2002, 115(14) 2809-16.
Nucifora et al., "Interference by huntingtin and atrophin-1 with cbp-mediated transcription leading to cellular toxicity," Science 2001, 291 (5512) 2423-8.
Orr et al., "Beyond the Qs in the polyglutamine diseases," Genes Dev, 15(8): 925-932, 2001.
Orrenius et al., "Regulation of cell death: the calcium-apoptosis link," Nat Rev Mol Cell Biol, 4: 552-565, 2003.
Pan et al., "Constructing optimum blood brain barrier QSAR models using a combination of 4D-molecular similarity measures and cluster analysis," J. Chem. Int. Com put. Sci. 2004, 44(6), 2083-98.
Parsell et al., "Protein disaggregation mediated by heat-shock protein Hsp104," Nature 1994, 372(6505), 475-8.
Pasinelli et al., "Molecular biology of amyotrophic lateral sclerosis: insights from genetics," Nat Rev Neurosci, 7(9): 710-723, 2006.
Perez et al., "Recruitment and the role of nuclear localization in polyglutamine-mediated aggregation," J Cell Biol, 143(6): 1457-1470, 1998.
Perutz et al., "Glutamine repeats and neurodegenerative diseases," Brain Res Bull, 50(5-6), 467, 1999.
Ping et al., "Apamin-sensitive Ca(2+)-activated K± channels regulate pacemaker activity in nigral dopamine neurons," Neuroreport, 7: 809-814, 1996.
Puopolo et al., "Roles of subthreshold calcium current and sodium current in spontaneous firing of mouse midbrain dopamine neurons," J Neurosci, 27: 645-656, 2007.
Ritz et al., "L-Type Calcium Channel blockers and Parkinson's Disease in Denmark," Annals Neurology, 67(5): 600-606; 2010.
Rizzuto et al., "Intracellular Ca(2+) pools in neuronal signalling," Curr Opin Neurobiol, 11: 306-311, 2001.
Romo et al., "Dopamine neurons of the monkey midbrain: contingencies of responses to active touch during self-initiated arm movements," J Neurophysiol, 63: 592-606, 1990.
Rose et al., "Modeling blood-brain barrier partitioning using the electrotopological state," J. Chem. Int. Comput. Sci. 2002, 42(3), 651-66.
Ross et al., "Intranuclear neuronal inclusions: a common pathogenic mechanism for glutamine-repeat neurodegenerative diseases?," Neuron, 19(6): 1147-1150, 1997.
Ross et al., "Polyglutamine pathogenesis: emergence of unifying mechanisms for Huntington's disease and related disorders," Neuron, 35(5): 819-822, 2002.
Rubinsztein, "The roles of intracellular protein-degradation pathways in neurodegeneration," Nature 2006, 443 (7113), 780-6.

(Continued)

*Primary Examiner* — Sarah Pihonak
*Assistant Examiner* — Jason Deck
(74) *Attorney, Agent, or Firm* — Casimir Jones SC; David W. Staple

(57) ABSTRACT

The present invention relates to compositions and methods for the treatment and/or prevention of neurodegenerative disorders, e.g., Parkinson's disease (PD). In particular, the present invention provides compositions comprising selective antagonists of calcium ion channels (e.g., cav1.3-type ion channels), and methods of use thereof to treat or prevent neurodegenerative disorders.

16 Claims, 14 Drawing Sheets

(56) References Cited

OTHER PUBLICATIONS

Sakahira et al., "Molecular chaperones as modulators of polyglutamine protein aggregation and toxicity," Proc. Natl. Acad. Sci. USA 2002, 99, 6412-8.
Saper et al., "Medullary catecholaminergic neurons in the normal human brain and in Parkinson's disease," Ann Neurol, 29: 577-584, 1991.
Schapira, "Mitochondria in the aetiology and pathogenesis of Parkinson's disease," Lancet Neurol, 7: 97-109, 2008.
Schroder et al., "DnaK, DnaJ and GrpE form a cellular chaperone machinery capable of repairing heat-induced protein damage," EMBO J. 1993, 12(11), 4137-44.
Sinnegger-Brauns et al., "Expression and 1,4-dihydropyridine-binding properties of brain L-type calcium channel isoforms," Mol Pharmacol,75: 407-414, 2009.
Sreedharan et al., "TDP-43 mutations in familial and sporadic amyotrophic lateral sclerosis," Science 2008, 319, 1668-1672.
Stenoien et al., "Polyglutamine-expanded androgen receptors form aggregates that sequester heat shock proteins, Drateasome components and SRC-1, and are suppressed by the HDJ-2 chaperone," Hum. Mol. Genet. 1999, 8(5), 731-41.
Suhr et al., "Identities of sequestered proteins in aggregates from cells with induced polyglutamine expression," J. Cell Biol. 2001, 153(2), 283-94.
Sulzer et al., "Multiple hit hypotheses for dopamine neuron loss in Parkinson's disease," Trends Neurosci, 30: 24450, 2007.
Tadross et al., "Molecular endpoints of Ca2+/calmodulin- and voltage-dependent inactivation of Ca(v)1.3 channels," J Gen Physiol, 135(3): 197-215, 2010.
Takeuchi et al., "Hsp70 and Hsp40 improve neurite outgrowth and suppress intracytoplasmic aggregate formation in cultured neuronal cells expressing mutant SOD1," Brain Res. 2002, 949(1-2), 11-22.
Taylor et al., "Toxic proteins in neurodegenerative disease," Science, 296(5575): 1991-1995, 2002.
Traynor et al., "Neuroprotective agents for clinical trials in ALS: a systematic assessment," Neurology. 2006, 67(1), 20-7.
Warrick et al., "Suppression of polyglutamine-mediated neurodegeneration in *Drosophila* by the molecular chaperone HSP70," Nat Genet. 1999, 23(4), 425-8.
Wegorzewska et al., "TDP-43 mutant transgenic mice develop features of ALS and frontotemporal lobar degeneration," Proc. Natl. Acad. Sci. USA 2009, 106(44), 18809-18814.
Westerheide et al., "Heat shock response modulators as therapeutic tools for diseases of protein conformation," J. Biol. Chem. 2005, 280(39), 33097-100.
Wils et al., "TDP-43 transgenic mice develop spastic paralysis and neuronal inclusions characteristic of ALS and frontotemporal lobar degeneration," Proc. Natl. Acad. Sci. USA 2010, 107(8), 3858-3863.
Wilson et al., "Coupled oscillator model of the dopaminergic neuron of the substantia nigra," J Neurophysiol, 83: 3084-3100, 2000.
Xia et al., Pyrimidine-2,4,6-trione derivatives and their inhibition of mutant SOD1-dependent protein aggregation. Toward a treatment for amyotrophic lateral sclerosis, J Med Chem, 54: 2409-2421, 2010.
Xu et al., "Neuronal Ca(V)1.3alpha(1) L-type channels activate at relatively hyperpolarized membrane potentials and are incompletely inhibited by dihydropyridines," J Neurosci, 21: 5944-5551, 2001.
Yokoseki et al., "TDP-43 mutation in familial amyotrophic lateral sclerosis," Ann. Neural. 2008, 63, 538-542.
Morimoto et al., "Stress-inducible responses and heat shock proteins: new pharmacologic targets for cytoprotection," Nat Biotechnol. 1998, 16(9), 833-8.
Van Den Eeden et al., Incidence of Parkinson's Disease: Variation by Age, Gender, and Race/Ethnicity, Am J Epidemiol 2003; 157:1015-1022.
Adenot et al., "Blood-brain barrier permeation models: discriminating between potential CNS and non-CNS drugs including P-glycoprotein substrates," J Chem Inf Comput Sci., 44(1):239-48, 2004.
Auluck et al., "Chaperone suppression of alpha-synuclein toxicity in a *Drosophila* model for Parkinson's disease," Science,2002, 295(5556), 865-8.
Bailey et al., "Molecular chaperones enhance the degradation of expanded polyglutamine repeat androgen receptor in a cellular model of spinal and bulbar muscular atrophy," Hum. Mol. Genet 2002, 11(5): 515-23.
Becker et al., "Use of antihypertensives and the risk of Parkinson disease," Neurology, 70: 1438-1444, 2008.
Berridge et al., "The versatility and universality of calcium signalling," Nat Rev Mol Cell Biol, 1: 11-21, 2000.
Bonci et al., "L-Type calcium channels mediate a slow excitatory synaptic transmission in rat midbrain dopaminergic neurons," J Neurosci, 18: 6693-6703, 1998.
Carmichael et al., "Bacterial and yeast chaperone reduce both aggregate formation and cell death in mammalian cell models of Huntington's disease," Proc. Natl. Acad. Sci. USA 2000, 97(17), 9701-5.
Chai et al., "Live-cell imagining reveals divergent intracellular dynamics of polyglutamine disease proteins and supports a sequestration model of pathogenesis," Proc. Natl. Acad. Sci. USA 2002, 99(14), 9310-5.
Chan et al., "Calcium homeostasis, selective vulnerability and Parkinson's disease," Trends Neurosci, 32: 249-256, 2009.
Chan et al., "'Rejuvenation' protects neurons in mouse models of Parkinson's disease," Nature, 447: 1081-1086, 2007.
Cummings et al., "Chaperone suppression of aggregation and altered subcellular proteasome localization imply protein misfolding in SCA1.," Nat Genet, 19(2): 148-154, 1998.
Damier et al., "The substantia nigra of the human brain. II. Patterns of loss of dopamine-containing neurons in Parkinson's disease," Brain, 122(Pt 8): 1437-1448, 1999.
Davies et al., "Formation of neuronal intranuclear inclusions underlies the neurological dysfunction in mice transgenic for the HD mutation," Cell, 90(3):537-548, 1997.
Di et al., "High throughput artificial membrane permeability assay for blood-brain barrier," Eur. J. Med. Chem. 2003, 38(3), 223-32.
Di et al., "Profiling drug-like properties in discovery research," Curr. Opin. Chem. Biol, 2003, 7(3) 402-8.
Difiglia et al., "Aggregation of huntingtin in neuronal intranuclear inclusions and dystrophic neurites in brain," Science, 277(5334): 1990-1993, 1997.
Fahn et al., "Does levodopa slow or hasten the rate of progression of Parkinson's disease?," J Neurol, 252(Suppl 4): IV37-IV42, 2005.
Gething, M.J. "Protein folding. The difference with prokaryote," Nature, 1997, 388(6640) 329,331.
Gidalevitz et al., "Progressive disruption of cellular protein folding in models of polyglutamine diseases," Science 2006, 311(5766) 1471-4.
Grace et al., "The control of firing pattern in nigral dopamine neurons: single spike firing," J Neurosci, 4:2866-2876, 1984.
Greenamyre et al., "Biomedicine. Parkinson's—divergent causes, convergent mechanisms," Science, 304: 1120-1122, 2004.
Guzman et al., "Robust pacemaking in substantia nigra dopaminergic neurons," J Neurosci, 29: 11011-11019, 2009.
Hartl, F.U., "Molecular chaperones in cellular protein folding," Nature 1996, 381 (6583) 571-9.
Hatab et al., "Synthesis of New 4-Substituted-3-a/koxy-2-butenoic Acid Esters and Pyrazo/e-3-one Derivatives," Jordan Journal of Chemistry, 2008, 3(3): 211-221.
Hitzel et al., "An increased throughput method for the determination of partition coefficients," Pharm. Res. 2000, 17(11):1389-95.
Horwich et al., "Deadly conformations-protein misfolding in prion disease," Cell, 1997, 89(4), 499-510.
Ikeda et al., "Expanded polyglutamine in the Machado-Joseph disease protein induces cell death in vitro and in vivo," Nat Genet, 13(2): 196-202, 1996.
International Search Report and Written Opinion for PCT/US09/06237 dated Jul. 22, 2010.
International Search Report and Written Opinion for PCT/US12/21896 dated May 16, 2012.

(56) References Cited

OTHER PUBLICATIONS

Ishihama et al., "A rapid method for pKa determination of drugs using pressure-assisted capillary electrophoresis with photodiode array detection in drug discovery," J. Pharm. Sci. 2002, 91 (4), 933-42.

Ito et al., "Synthesis of Pyrazolone Derivatives. XX. On the Cyclization of 4-Bromo-3-(2-formamidopheny/)thiomethy/-2-methy/-1-pheny/-3-pyrazo/in-5 one," Journal of the Pharmaceutical Society of Japan, 1973, 93(2): 207-213.

Ito et al., "Calbindin-D28k in the basal ganglia of patients with parkinsonism," Ann Neural, 32: 543-550, 1992.

Jana et al., "Altered proteasomal function due to the expression of polyglutamine-expanded truncated N-terminal huntingtin induces apoptosis by caspase activation through mitochondral cytochrome c release," Hum. Mol. Genet. 2001, 10(10), 1049-59.

Johnson et al., "TDP-43 is intrinsically aggregation-prone, and amyotrophic lateral sclerosis-linked mutations accelerate aggregation and increase toxicity," J. Biol. Chem. 2009, 284(30), 20329-20339.

Kabashi et al., "TARDBP mutations in individuals with sporadic and familial amyotrophic lateral sclerosis," Nature Genetics 2008, 40(5), 572-574.

Kassel, D. B., "Applications of high-throughput ADME in drug discovery,"Curr. Opin. Chem. Biol. 2004, 8(3), 339-45.

Kazantsev et al., "Insoluble detergent-resistant aggregates form between pathological and nonpathological lengths pf polyglutamine in mammalian cells," Proc Natl Acad Sci USA, 96(20): 11404-11409, 1999.

Kazemi-Esfarjani et al., "Genetic suppression of polyglutamine toxicity in Drosophila," Science 2000, 287(5459), 1837-40.

Kazemi-Esfarjani et al.,"Suppression of polyglutamine toxicity by a Drosophila homolog of myeloid leukemia factor 1," Hum. Mol. Genet 2002, 11(21):2657-72.

Kerns et al., "Multivariate pharmaceutical profiling for drug discovery," Curr. Top. Med. Chem. 2002, 2(1), 87-98.

Kieran et al., "Treatment with arimoclomol, a coinducer of heat shock proteins, delays disease progression in ALS mice," Nat Med. 2004, 10(4):402-5.

Kim et al., "Polyglutamine protein aggregates are dynamic," Nat. Cell Biol. 2002, 4(10), 826-31.

Kish et al., "Uneven pattern of dopamine loss in the striatum of patients with idiopathic Parkinson's disease. Pathophysiologic and clinical implications," N Engl J Med, 318: 876-880, 1988.

Koo et al., "Amyloid diseases: abnormal protein aggregation in neurodegeneration," Proc Natl Acad Sci USA, 96(18): 9989-9990, 1999.

Kopito et al., "Conformational disease," Nat Cell Bio, 2(11): E207-209, 2000.

Kwong et al., "TDP-43 proteinopathy: the neuropathology underlying major forms of sporadic and familial frontotemporal lobar degeneration and motor neuron disease," Acta Neuropath. 2007, 114, 63-70.

Lansbury et al., "A century-old debate on protein aggregation and neurodegeneration enters the clinic," Nature 2006, 443(7113), 774-9.

MacKenzie et al., "Pathological TDP-43 distinguishes sporadic amyotrophic lateral sclerosis from amyotrophic lateral sclerosis with SOD1 mutations," Ann. Neurol. 2007, 61(5), 427-434.

Matsumoto et al., "Huntingtin and mutant SOD1 form aggregate structures with distinct molecular properties in human cells," J. Biol. Chem. 2005, 281(7), 4477-4485.

Matzuk et al., "Preservation of hypothalamic dopaminergic neurons in Parkinson's disease," Ann Neurol, 18: 552-555, 1985.

R1 is cycloalkyl
R2 is substituted 2-phenylethyl

SKP004C08
IC$_{50}$: 1.61 µM
Selectivity: >1000

SKP004C07
IC$_{50}$: 0.89 µM
Selectivity: >100

SKP003E07
IC$_{50}$: 1.15 µM
Selectivity: >100

SKP004A07
IC$_{50}$: 2.18 µM
Selectivity: >100

SKP005C06
IC$_{50}$: 0.15µM
Selectivity: 4

SKP004E02
IC$_{50}$: 0.18µM
Selectivity: 44

SKP004E02
IC$_{50}$: 0.28µM
Selectivity: 22

A  3-(4-clorobenzylthio)-4-ethyl-5-phenyl-1,2,4-triazole
(thiotriazole)

B  1,3-bis(4-chlorophenethyl)pyrimidine-2,4,6-trione
(PYT)

SELECTIVE CALCIUM CHANNEL ANTAGONISTS

CROSS-REFERENCE TO RELATED APPLICATION

The present invention is a continuation of U.S. patent application Ser. No. 13/354,156, filed Jan. 19, 2012, now U.S. Pat. No. 9,428,467, which claims priority to U.S. Provisional Patent Application Ser. No. 61/434,044, filed Jan. 19, 2011, each of which is herein incorporated by reference in their entireties.

FIELD OF THE INVENTION

The present invention relates to compositions and methods for the treatment and/or prevention of neurodegenerative disorders, e.g., Parkinson's disease (PD). In particular, the present invention provides compositions comprising selective antagonists of calcium ion channels (e.g., Cav1.3-type ion channels), and methods of use thereof to treat or prevent neurodegenerative disorders.

BACKGROUND OF THE INVENTION

Parkinson's disease (PD) is the second most common neurodegenerative disease in the developed world. Age is the strongest risk factor in PD with incidence rising exponentially after 65 (Caine & Langston. (1983) Lancet, 2, 1457-9.; de Lau et al. (2004) Neurology, 63, 1240-4.; herein incorporated by reference in their entireties). Because improvements in health care are increasing life expectancy, the number of PD patients is expected to grow dramatically in the coming years, reaching over 2 million in the U.S. by 2025 (Dorsey et al. (2007) Neurology, 68, 384-6.; herein incorporated by reference in its entirety). This is expected to have an enormous economic cost, reaching over 50 billion dollars per year by 2025.

Although there are signs of distributed neuropathology in PD (as judged by LB formation) (Braak et al., 2004), the motor symptoms, including bradykinesia, rigidity, and resting tremor, are clearly linked to the degeneration and death of SNc DA neurons (Hornykiewicz. (1966) Pharmacol Rev, 18, 925-64.; Riederer & Wuketich. (1976) J Neural Transm, 38, 277-301.; herein incorporated by reference in their entireties). The palliative efficacy of L-DOPA—a DA precursor—is testament to the centrality of these neurons in the motor symptoms of PD.

The factors governing the loss of substantia nigra pars *compacta* (SNc) dopamine (DA) neurons have been the subject of speculation for decades. DA itself has long been viewed as a culprit, as oxidation of cytosolic DA, and its metabolites, is damaging (Greenamyre & Hastings. (2004) Science, 304, 1120-2.; Sulzer. (2007) Trends Neurosci, 30, 24450.; herein incorporated by reference in their entireties). However, there are reasons to doubt this type of cellular stress alone is responsible for the loss of DA neurons in PD. First, there is considerable regional variability in the vulnerability of DA neurons in PD, with some being devoid of pathological markers (Matzuk & Saper. (1985) Ann Neurol, 18, 552-5.; Kish et al. (1988) N Engl J Med, 318, 876-80.; Saper et al. (1991) Ann Neurol, 29, 577-84.; Ito et al. (1992) Ann Neurol, 32, 543-50.; Damier et al. (1999) Brain, 122 (Pt 8), 1437-48.; herein incorporated by reference in their entireties). Second, L-DOPA administration, which relieves symptoms by elevating DA levels in PD patients, does not appear to accelerate disease progression, suggesting that DA is not a significant source of reactive oxidative stress, at least in the short term (Fahn. (2005) J Neurol, 252 Suppl 4, IV37-IV42.; herein incorporated by reference in its entirety). Calcium entry through L-type channels has been shown to stimulate DA metabolism in SNc DA neurons, pushing cytosolic DA concentrations into a toxic range with L-DOPA loading (Mosharov et al. (2009) Neuron, 62, 218-29.; herein incorporated by reference in its entirety). However, the frank death or degeneration of a variety of non-dopaminergic neurons in PD argues that DA itself is not likely to be the principal cell autonomous risk factor in the disease.

Unlike the vast majority of neurons in the brain, adult SNc DA neurons are autonomously active, generating regular, broad action potentials (2-4 Hz) in the absence of synaptic input (Grace & Bunney. (1984) J Neurosci, 4, 2866-76.; Nedergaard et al. (1993) J Physiol, 466, 727-47.; Guzman et al. (2009) J Neurosci, 29, 11011-9.; Chan et al. (2007) Nature, 447, 1081-6.; herein incorporated by reference in their entireties). This pace making activity is believed to be important to maintaining ambient DA levels in regions that are innervated by these neurons, particularly the striatum (Romo & Schultz. (1990) J Neurophysiol, 63, 592-606.; herein incorporated by reference in its entirety). While most neurons rely exclusively on monovalent cation channels to drive pacemaking, SNc DA neurons also engage L-type ion channels that allow calcium to enter the cytoplasm (Ping & Shepard. (1996) Neuroreport, 7, 809-14.; Bonci et al. (1998) J Neurosci, 18, 6693-703.; Puopolo et al. (2007) J Neurosci, 27, 645-56.; herein incorporated by reference in their entireties), leading to oscillations in intracellular calcium concentrations (Guzman et al. (2009) J Neurosci, 29, 11011-9.; Chan et al. (2007) Nature, 447, 1081-6.; Wilson & Callaway. (2000) J Neurophysiol, 83, 3084-100.; herein incorporated by reference in their entireties). The L-type calcium channels used by SNc DA neurons in pacemaking have a distinctive Cav1.3 pore-forming subunit encoded by Cacna1d. Cav1.3 calcium channels are relatively rare, constituting only about 10% of all the L-type calcium channels found in the brain. Channels with this subunit differ from other L-type calcium channels in that they open at relatively hyperpolarized potentials (Xu & Lipscombe. (2001) J Neurosci, 21, 5944-51.; herein incorporated by reference in its entirety), allowing them to contribute to the mechanisms driving the membrane potential to action potential threshold underlying autonomous pacemaking.

The sustained engagement of Cav1.3 calcium channels during pace making comes at an apparent metabolic cost to SNc DA neurons. Because of its involvement in cellular processes ranging from the regulation of enzyme activity to programmed cell death, calcium is under very tight homeostatic control, with a cytosolic set point near 100 nM-10,000 times lower than the concentration of calcium in the extracellular space (Berridge et al. (2000) Nat Rev Mol Cell Biol, 1, 11-21.; Rizzuto. (2001) Curr Opin Neurobiol, 11, 306-11.; Orrenius et al. (2003) Nat Rev Mol Cell Biol, 4, 552-65.; herein incorporated by reference in their entireties). Calcium entering neurons is rapidly sequestered or pumped back across the steep plasma membrane concentration gradient; this process requires energy stored in adenosine triphosphate (ATP) or in ion gradients that are maintained with ATP-dependent pumps, like the Na-K ATPase. In most neurons, calcium channel opening is a rare event, occurring primarily during very brief action potentials. This makes the metabolic cost to the cell readily manageable. But in SNc DA neurons, where Cav1.3 calcium channels are open much of the time, the magnitude and the spatial extent of calcium influx are much larger. Transgenic mice that express a mitochondrially targeted redox-sensitive variant of green fluorescent protein (mito-roGFP) under control of the tyrosine hydroxylase promoter have revealed that indeed mitochodria in SNc DA neurons have a high basal oxidant stress that is a direct consequence of opening of L-type calcium channels. Furthermore, calcium entry (and presumably the concomitant oxidant stress) increases the vulnerability of SNc DA neurons to toxins (MPTP, 6-hydroxydopamine (6-OHDA), rotenone) used to create animal models of PD.

These results indicate that calcium entry during pace making elevates mitochondrial oxidant stress in SNc DA neurons and increases their vulnerability to toxins and genetic mutations with metabolic consequences. This oxidant stress also should increase the rate of cellular aging and death. This physiological model of vulnerability in PD and other aging related neurodegenerative diseases extends beyond SNc DA neurons to ex-plain the loss of many of the other neuronal populations lost in the disease, including neurons of the locus ceruleus, raphe nuclei, hypothalamus, and penduculopontine nucleus.

Epidemiological studies have shown that use of dihydropyridines that cross the blood-brain barrier are associated with a significant reduction in the risk of developing Parkinson's disease. The utility of these compounds is limited by their cardiovascular side-effects, which are attributable to their antagonism of Cav1.2 channels in heart and vascular smooth muscle. Due to their affinity for Cav1.2 channels, at higher doses, dihydropyridines induce hypotension and cardiac failure. This severely limits their utility as a neuroprotective agent. What is needed are pharmacological agents that preferentially antagonize calcium channels with a Cav1.3 pore, the type of channels responsible for neurodegeneration in PD.

SUMMARY OF THE INVENTION

The present invention relates to compositions and method for the treatment and/or prevention of PD and/or other neurodegenerative diseases or disorders. In some embodiments, pyrimidine-2,4,6-trione compounds (PYT compounds), derivatives thereof, and pharmaceutical compositions thereof are provided to treat neurodegenerative diseases (e.g., PD). Among other things, the present invention provides methods of treating PD with provided PYT compounds. Without being be bound by any particular theory, provided PYT compounds are useful in the treatment of PD or other neurodegenerative diseases where Cav1.3 calcium channels are implicated and/or play a causative role.

In some embodiments, the present invention provides a composition (e.g., for treating PD or other neurodegenerative diseases) comprising a Cav1.3-selective calcium ion channel antagonist. In some embodiments, a Cav1.3-selective calcium ion channel antagonist comprises a compound of the formula:

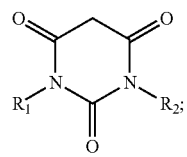

wherein R1 comprises a cycloalkane or bicycloalkane, and R2 comprises a substituted aryl ring group. In some embodiments, R1 comprises cyclohexane, cyclopentane, or bicyclo [2.2.1]heptanes (norbornane). In some embodiments, R2 comprises a substituted phenyl group. In some embodiments, the phenyl group comprises a single non-hydrogen substituent selected from the group consisting of: F, Cl, Br, $CF_3$, $CO_2H$, CN, $NO_2$, MeO, and Me. In some embodiments, the substituent is selected from the group consisting of: Cl, $CF_3$, and Me.

In some embodiments, the present invention provides a compound of the formula:

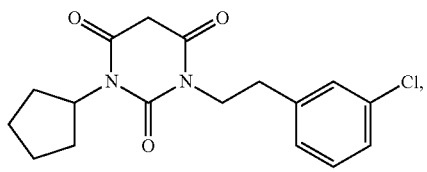 [SMILES: O=C1CC(=O)N(C2CCCC2)C(=O)N1CCc1cccc(Cl)c1]

or derivatives thereof.

In some embodiments, the present invention provides a compound of the formula:

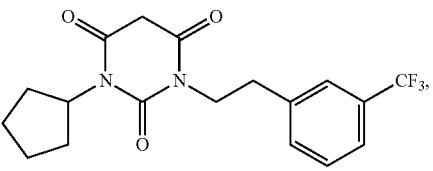 [SMILES: O=C1CC(=O)N(C2CCCC2)C(=O)N1CCc1cccc(C(F)(F)F)c1]

or derivatives thereof.

In some embodiments, the present invention provides a compound of the formula:

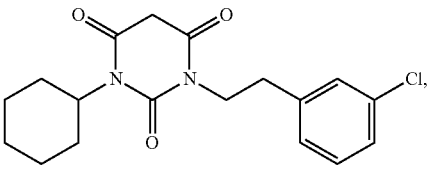

or derivatives thereof.

In some embodiments, the present invention provides a compound of the formula:

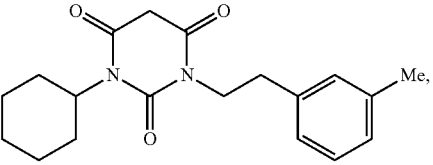 [SMILES: Cc1cccc(CCN2C(=O)CC(=O)N(C3CCCCC3)C2=O)c1]

or derivatives thereof.

In some embodiments, the present invention provides a compound of the formula:

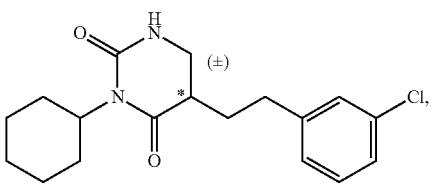 [SMILES: O=C1NCC(CCc2cccc(Cl)c2)C(=O)N1C1CCCCC1]

or derivatives thereof.

In some embodiments, the present invention provides a compound of the formula:

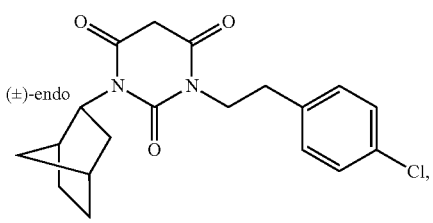 [SMILES: O=C1CC(=O)N(C2CC3CCC2C3)C(=O)N1CCc1ccc(Cl)cc1]

or derivatives thereof.

In some embodiments, the present invention provides a compound of the formula:

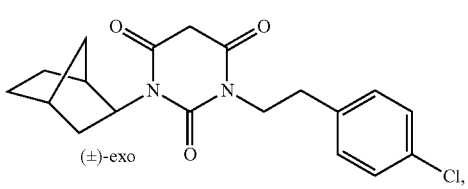 [SMILES: O=C1CC(=O)N(C2CC3CCC2C3)C(=O)N1CCc1ccc(Cl)cc1]

or derivatives thereof.

In some embodiments, the present invention provides a method of treating and/or preventing a neurodegenerative disorder comprising administering a Cav1.3-selective calcium ion channel antagonist to a subject. In some embodiments, a Cav1.3-selective calcium ion channel antagonist comprises a compound of the present invention. In some embodiments, a neurodegenerative disorder comprises Parkinson's disease. In some embodiments, a neurodegenerative disorder comprises Alzheimer's disease. In some embodiments, a subject suffers from a neurodegenerative disorder. In some embodiments, a subject has one or more risk factors for a neurodegenerative disorder. In some embodiments, risk factors for a neurodegenerative disorder comprise: increased age (e.g., >40, >50, >60, >70, >80, etc.), genetic polymorphisms linked to neurodegenerative disorders, environmental factors, gender, education, endocrine conditions, oxidative stress, inflammation, stroke, hypertension, diabetes, smoking, head trauma, depression, infection, tumors, vitamin deficiencies, immune and metabolic conditions, and chemical exposure. In some embodiments, the subject is not administered a dopamine agonist.

In some embodiments, the present invention provides a method of selectively inhibiting a Cav1.3 calcium ion channel (e.g., for treating PD or other neurodegenerative diseases) comprising contacting the Cav1.3 calcium ion channel with a Cav1.3-selective antagonist. In some embodiments, a Cav1.3-selective antagonist comprises a compound of the formula:

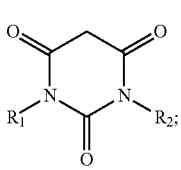

wherein R1 comprises a cycloalkane or bicycloalkane, and R2 comprises a substituted aryl ring group. In some embodiments, R1 comprises cyclohexane, cyclopentane, or bicyclo[2.2.1]heptanes (norbornane). In some embodiments, R2 comprises a substituted phenyl group. In some embodiments, the phenyl group comprises a single non-hydrogen substituent selected from the group consisting of: F, Cl, Br, $CF_3$, $CO_2H$, CN, $NO_2$, MeO, and Me. In some embodiments, the substituent is selected from the group consisting of: Cl, $CF_3$, and Me.

In some embodiments, the present invention provides a method of selectively inhibiting a Cav1.3 calcium ion channel (e.g., for treating PD or other neurodegenerative diseases) comprising contacting the Cav1.3 calcium ion channel with a compound of the formula:

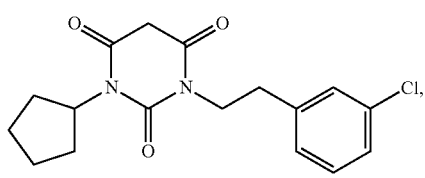 [SMILES: O=C1CC(=O)N(C2CCCC2)C(=O)N1CCc1cccc(Cl)c1]

or derivatives thereof.

In some embodiments, the present invention provides a method of selectively inhibiting a Cav1.3 calcium ion channel (e.g., for treating PD or other neurodegenerative diseases) comprising contacting the Cav1.3 calcium ion channel with a compound of the formula:

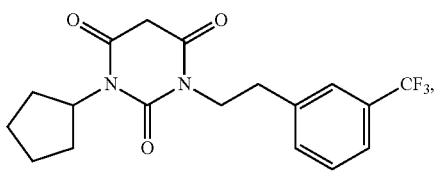 [SMILES: O=C1CC(=O)N(C2CCCC2)C(=O)N1CCc1cccc(C(F)(F)F)c1]

or derivatives thereof.

In some embodiments, the present invention provides a method of selectively inhibiting a Cav1.3 calcium ion channel (e.g., for treating PD or other neurodegenerative diseases) comprising contacting the Cav1.3 calcium ion channel with a compound of the formula:

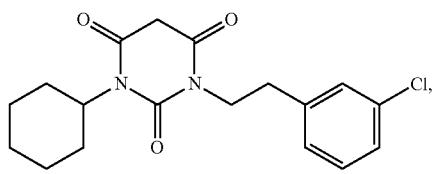 [SMILES: O=C1CC(=O)N(C2CCCCC2)C(=O)N1CCc1cccc(Cl)c1]

or derivatives thereof.

In some embodiments, the present invention provides a method of selectively inhibiting a Cav1.3 calcium ion channel (e.g., for treating PD or other neurodegenerative diseases) comprising contacting the Cav1.3 calcium ion channel with a compound of the formula:

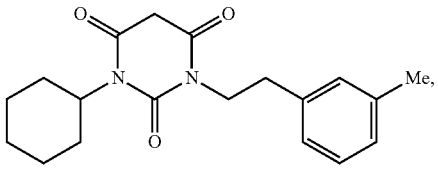 [SMILES: Cc1cccc(CCN2C(=O)CC(=O)N(C3CCCCC3)C2=O)c1]

or derivatives thereof.

In some embodiments, the present invention provides a method of selectively inhibiting a Cav1.3 calcium ion channel (e.g., for treating PD or other neurodegenerative diseases) comprising contacting the Cav1.3 calcium ion channel with a compound of the formula:

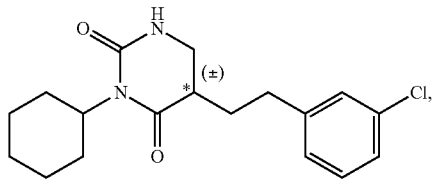 [SMILES: O=C1NCC(CCc2cccc(Cl)c2)C(=O)N1C1CCCCC1]

or derivatives thereof.

In some embodiments, the present invention provides a method of selectively inhibiting a Cav1.3 calcium ion channel (e.g., for treating PD or other neurodegenerative diseases) comprising contacting the Cav1.3 calcium ion channel with a compound of the formula:

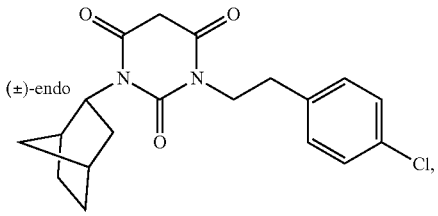 [SMILES: O=C1CC(=O)N(C2CC3CCC2C3)C(=O)N1CCc1ccc(Cl)cc1]

or derivatives thereof.

In some embodiments, the present invention provides a method of selectively inhibiting a Cav1.3 calcium ion channel (e.g., for treating PD or other neurodegenerative diseases) comprising contacting the Cav1.3 calcium ion channel with a compound of the formula:

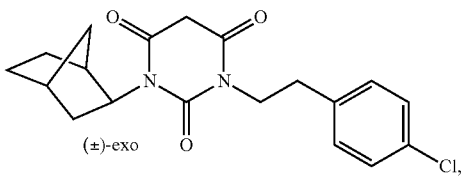 [SMILES: O=C1CC(=O)N(C2CC3CCC2C3)C(=O)N1CCc1ccc(Cl)cc1]

or derivatives thereof.

In some embodiments, the present invention provides kits and/or systems comprising one or more Cav1.3-selective antagonists and one or more other compounds for the treatment of PD and/or other neurodegenerative diseases. In some embodiments, the present invention provides systems comprising one or more Cav1.3-selective antagonists within a delivery device. In some embodiments, a delivery device comprises a pill, capsule, needle, etc.

DEFINITIONS

Figure 1:
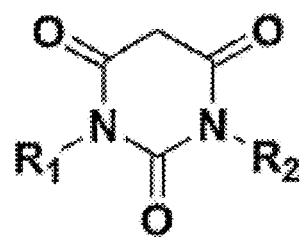
FIG. 1 shows the general structure of exemplary PYT analogues.

As used herein, the term "antagonist" refers to any molecule that is capable of blocking or decreasing the amount of ligand binding to a receptor. An antagonist may decrease receptor/ligand binding by interacting with either the receptor or ligand. An antagonist is capable of diminishing or abolishing receptor/ligand interactions.

As used herein, the term "selective antagonist" refers to an antagonist having greater affinity for its target than for one or more related receptors. For example, a "Cav1.3-selective antagonist" has greater affinity for Cav1.3 than for one or more similar calcium-ion channels (e.g., other Cav1 or L-type family members (e.g., Cav1.2). The greater affinity of its target may be, for example, at least: 1.1-fold, 1.2-fold, 1.3-fold, 1.4-fold, 1.5-fold . . . 2-fold . . . 3-fold . . . 4-fold . . . 5-fold . . . 10-fold . . . 20-fold . . . 50-fold . . . $10^2$-fold . . . $10^3$-fold . . . $10^5$-fold . . . $10^5$-fold, etc.

As used herein, the term "aliphatic" or "aliphatic group", refers to a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C3-C6 hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). In some embodiments, use of the term "about" in reference to dosages means±5 mg/kg/day.

As used herein, the term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

As used herein, the terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl). In some embodiments, a heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "subject" refers to any organism to which provided PYT compound is administered in accordance with the present invention e.g., for experimental, diagnostic, prophylactic, and/or therapeutic purposes. Typical subjects include animals (e.g., mammals such as mice, rats, rabbits, non-human primates, and humans; insects; worms; etc.). In some embodiments, a subject may be suffering from, at risk of and/or susceptible to a disease, disorder, and/or condition (e.g., a neurodegenerative disease, a disease, PD, AD, etc.). In some embodiments, the term "patient" is used to refer to a human subject.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In some embodiments, the term "PYT compound" may encompass prodrugs and/or esters of compounds of the pyrimidine 2,4,6 triones described herein. PYT compounds may be provided in salt form. In particular, in some embodiments, a PYT compound is provided as a pharmaceutically acceptable salt. The provided PYT compounds may exist in particular geometric or stereoisomeric forms. The present invention contemplates all such PYT compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. In certain embodiments, the present invention relates to a PYT compound represented by any of the structures outlined herein, wherein the compound is a single stereoisomer.

Contemplated equivalents of the compounds described above include compounds which otherwise correspond thereto, and which have the same general properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants, which are in themselves known, but are not mentioned here.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

An individual who is "suffering from" a disease, disorder, and/or condition has been diagnosed with and/or displays one or more symptoms of a disease, disorder, and/or condition.

An individual who is "susceptible to" or "at risk of" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

As used herein, the term "treat," "treatment," or "treating" refers to any method used to partially or completely alleviate, ameliorate, relieve, inhibit, prevent, delay

DETAILED DESCRIPTION OF THE INVENTION

The present invention relates to compositions and methods for the treatment and/or prevention of neurodegenerative disorders, e.g., Parkinson's disease (PD). In particular, the present invention provides compositions comprising selective antagonists of calcium ion channels (e.g., cav1.3-type ion channels), and methods of use thereof to treat or prevent neurodegenerative disorders. In some embodiments, the present invention provides compositions comprising pyrimidine 2,4,6 triones, derivities thereof, and related compounds as selective antagonists of Cav1.3 channels and as treatment or prevention of neurodegenerative disorders, including, but not limited to PD and Alzheimer's disease (AD). In some embodiments, the present invention provides compositions (e.g., pyrimidine 2,4,6 triones, derivities thereof, and related compounds) that serve as neuroprotectives agent against PD, AD, and other aging-related neurodegenerative diseases.

Studies of the most vulnerable population of neurons in PD—substantia nigra pars *compacta* (SNc) dopamine (DA) neurons—have revealed that they have a distinctive physiological phenotype that leads to a sustained elevation in mitochondrial oxidant stress (Chan & Surmeier. (2009) Trends Neurosci, 32, 249-56.; herein incorporated by reference in its entirety). Mitochondrial oxidant stress has long been viewed as a major factor in PD (Schapira. (2008) Lancet Neurol, 7, 97109.; herein incorporated by reference in its entirety). This mitochondrial stress originates from a sustained calcium influx through a distinctive voltage-dependent channel in the plasma membrane of SNc dopamine neurons. This channel is a member of the Cav1 or L-type family. Antagonism of these channels protects SNc dopamine neurons in animal models of PD (Chan et al. (2007) Nature, 447, 1081-6.; herein incorporated by reference in its entirety). Epidemiological studies have shown that use of dihydropyridine antagonists of these channels significantly diminishes the risk of PD in humans (Becker et al. (2008) Neurology, 70, 1438-44.; Ritz et al. (2010) Annals Neurology.; herein incorporated by reference in their entireties). The obstacle against the use of dihydropyridine antagonists of these channels is that dihydropyridines preferentially bind to Cav1.2 calcium channels, which are found throughout the body, including the cardiovascular system (Sinnegger-Brauns et al. (2009) Mol Pharmacol, 75, 407-14.; herein incorporated by reference in its entity). Due to their affinity for Cav1.2 channels, at higher doses, dihydropyridines induce hypotension and cardiac failure. This severely limits their utility as a neuroprotective agent.

In some embodiments, the present invention provides compositions (e.g., antagonists) that prevent or treat neurodegenerative disorders (e.g. PD, AD, etc.) by selectively inhibiting the activity of one or more calcium-ion channels (e.g, Cav1.3). In some embodiments, compositions are antagonists of calcium-ion channels (e.g, Cav1.3) that are causative and/or involved in regulating processes of neurodegenerative disorders (e.g. AD, PD, etc.). In some embodiments, compositions are antagonists of calcium-ion channels (e.g, Cav1.3) that are causative and/or involved in regulating processes of Parkinson's disease. In some embodiments, provided herein are Cav1.3-selective inhibitors. In some embodiments, Cav1.3-selective inhibitors have greater affinity for Cav1.3 than for other Cav1 or L-type family members (e.g., Cav1.2). In some embodiments, Cav1.3-selective inhibitors have greater affinity for Cav1.3 than for one or more other Cav1 or L-type family members (e.g., Cav1.2). In some embodiments, Cav1.3-selective inhibitors have greater affinity for Cav1.3 than for Cav1.2. In some embodiments, Cav1.3-selective inhibitors exhibit at least 2-fold selectivity (e.g. 2-fold selectivity . . . 3-fold selectivity . . . 4-fold selectivity . . . 5-fold selectivity . . . 10-fold selectivity . . . 20-fold selectivity . . . 50-fold selectivity . . . 100-fold selectivity . . . 200-fold selectivity . . . 500-fold selectivity . . . 1000-fold selectivity . . . $10^4$-fold selectivity . . . $10^5$-fold selectivity . . . $10^6$-fold selectivity, etc.).

In some embodiments, the present invention provides selective molecular antagonists of Cav1.3. In some embodiments, compositions of the present invention comprise one or more antagonists that selectively bind to Cav1.3 (e.g., over Cav1.2, over other Cav1 or L-type family members, etc.). In some embodiments, antagonists are substituted pyrimidines (e.g., ketone substituted) and derivatives thereof. In some embodiments, an antagonist comprises a pyrimidine scaffold with one or more (e.g., 1, 2, 3, 4, 5, 6, etc.) substituents or functional groups. In some embodiments, a pyrimidine scaffold is substituted with one or more ketones (e.g., 1, 2, 3, 4, etc.). In some embodiments, a pyrimidine scaffold is tri-substituted with ketones (e.g. 2,4,6-substituted). In some embodiments, an antagonist comprises pyrimidine-2,4,6-trione, or derivatives thereof. In some embodiments, an antagonist comprises a pyrimidine-2,4,6-trione with one or more (e.g., 1, 2, 3, etc.) substituent groups (e.g. attached to ring-nitrogens and/or ring-carbons). In some embodiments, a pyrimidine-2,4,6-trione scaffold is substituted at one or both ring-nitrogens. In some embodiments, ring nitrogens are substituted with any suitable functional group, including, but not limited to: alkyl groups (e.g, straight chain or branched), substituted alkyl groups, cycloalkyl groups, substituted cycloalkyl groups, cycloaliphatic groups, substituted cycloaliphatic groups, aromatic groups, substituted aromatic groups (e.g., substituted with electron-withdrawing groups (e.g., F, Cl, Br, $CF_3$, $CO_2H$, CN, $NO_2$, etc.), substituted with electron donating groups (e.g., MeO, Me, etc.).

In some embodiments, the present invention provides selective molecular antagonists of Cav1.3. In some embodiments, compositions of the present invention comprise one or more antagonists that selectively bind to Cav1.3 (e.g., over Cav1.2, over other Cav1 or L-type family members, etc.). In some embodiments, antagonists are substituted cycloalkanes and derivatives thereof. In some embodiments, cycloalkanes comprise one or more (e.g., 1, 2, 3, etc.) atomic substitutions within the ring structure (e.g. oxygen substitutions, nitrogen substitutions, etc.). In some embodiments, cycloalkanes comprise one or more (e.g., 1, 2, 3, etc.) substituents or functional groups attached to the ring structure. In some embodiments, an antagonist comprises a ring scaffold (e.g., 3 member ring, 4 member ring, 5-member ring, 6 member ring, etc.). In some embodiments, an antagonist comprises a 6-member ring comprising carbon and nitrogen. In some embodiments, antagonists comprise a cyclohexane scaffold with atomic substitutions (e.g. oxygen substitutions, nitrogen substitutions, etc.) at the 1-, 2-, 3-, 4-, 5-, or 6-positions. In some embodiments, antagonists comprise a cyclohexane scaffold with one or more (e.g., 1, 2, 3, etc.) substituents or functional groups attached to the ring structure (e.g., at the 1-, 2-, 3-, 4-, 5-, or 6-positions). In some embodiments, an antagonist comprises a 6-member ring with nitrogens at the 1- and 3-positions (and carbons at the other positions). In some embodiments, an antagonist comprises a 6-member ring with substituents at the 1-, 2-, 3-, 4-, 5-, or 6-positions. In some embodiments, an antagonist comprises a 6-member ring with one or more (1, 2, 3, 4, 5, 6) ketone substitutents (e.g., at the 2-, 4-, and/or 6-positions). In some embodiments, an antagonist comprises a 6-member ring with nitrogens at the 1- and 3-positions and ketones at the 2-, 4-, and 6-positions.

In some embodiments, antagonists comprise a molecular structure according to the formula:

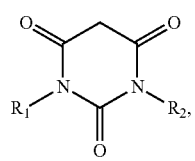

wherein $R_1$ and $R_2$ are any suitable substituents and/or functional groups. In some embodiments, $R_1$ and $R_2$ are selected from, but not limited to: alkyl groups (e.g, straight chain or branched), substituted alkyl groups, cycloalkyl groups, substituted cycloalkyl groups, cycloaliphatic groups, substituted cycloaliphatic groups, aromatic groups, substituted aromatic groups (e.g., substituted with electron-withdrawing groups (e.g., F, Cl, Br, $CF_3$, $CO_2H$, CN, $NO_2$, etc.), substituted with electron donating groups (e.g., MeO, Me, etc.). In some embodiments, an antagonist is hetero-substituted at $R_1$ and $R_2$ (i.e., $R_1$ and $R_2$ consist of different functional groups). In some embodiments, an antagonist is homo-substituted at $R_1$ and $R_2$ (i.e., $R_1$ and $R_2$ consist of the same functional groups). In some embodiments, $R_1$ and/or $R_2$ comprise a substituted or unsubstituted cycloalkyl or cycloaliphatic group (e.g. cyclohexane, cyclopentane, etc.). In some embodiments, $R_1$ and/or $R_2$ comprise substituted or unsubstituted cyclohexane. In some embodiments, $R_1$ and/or $R_2$ comprise substituted or unsubstituted cyclopentane. In some embodiments, $R_1$ and/or $R_2$ comprise substituted or unsubstituted aromatic ring structures (e.g., benzene, pyridine, furan, pyrrole, thiophene, isobenzofuran, indole, imidazole, benzofuran, isoindole, benzothiophene, indazole, naphthalene, quinoline, pyrimidine, acridine, etc.). In some embodiments, $R_1$ and/or $R_2$ comprise substituted or unsubstituted aromatic ring structures linked to the primary ring (i.e. scaffold ring) by any acceptable linker (e.g., alkyl chain (e.g., methyl, ethyl, propyl, butyl, etc.)). In some embodiments, $R_1$ and/or $R_2$ comprise a substituted phenyl ring. In some embodiments, $R_1$ and/or $R_2$ comprise a phenyl ring linked to the primary ring (i.e. scaffold ring) by any acceptable linker (e.g., alkyl chain (e.g., methyl, ethyl, propyl, butyl, etc.)). In some embodiments, $R_1$ and/or $R_2$ comprise a phenyl ring substituted at the 2-, 3-, 4-, 5-, and/or 6-positions. In some embodiments, $R_1$ and/or $R_2$ comprise a substituted 2-phenyl ring. In some embodiments, $R_1$ and/or $R_2$ comprise substituted 2-phenylethyl. In some embodiments, $R_1$ and/or $R_2$ comprise a phenyl group, linked to the primary ring (i.e. scaffold ring) by an ethyl group. In some embodiments, $R_1$ and/or $R_2$ comprise a phenyl group, substituted at the 2-position by an electron-withdrawing group (e.g., F, Cl, Br, $CF_3$, $CO_2H$, CN, $NO_2$, etc.) or electron donating group (e.g., MeO, Me, etc.). In some embodiments, $R_1$ and/or $R_2$ comprise 2-phenylethyl, wherein the substitutent at the 2-position is an electron-withdrawing group (e.g., F, Cl, Br, $CF_3$, $CO_2H$, CN, $NO_2$, etc.) or electron donating group (e.g., MeO, Me, etc.).

In some embodiments, antagonists comprise a molecular structure according to the formula:

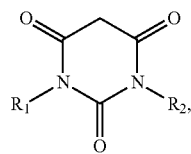

wherein $R_1$ comprises a cycloalkyl group, and $R_2$ comprises a substituted aromatic. In some embodiments, $R_1$ comprises cyclopropane, pyclobutane, cyclopentane, or cyclohexane. In some embodiments, $R_2$ comprises a substituted phenyl group. In some embodiments, $R_2$ comprises a substituted phenyl group attached to the primary ring (e.g. scaffold ring) by an alkyl chain (e.g., methyl, ethyl, propyl, butyl, etc.). In some embodiments, $R_2$ comprises a substituted phenyl group attached to the primary ring (e.g. scaffold ring) by an ethyl group. In some embodiments, $R_2$ comprises substituted 2-phenylethyl, wherein the ethyl group connects the phenyl ring and the primary ring (e.g. scaffold ring). In some embodiments, $R_2$ comprises substituted 2-phenylethyl, wherein the substituent comprises an electron-withdrawing group (e.g., F, Cl, Br, $CF_3$, $CO_2H$, CN, $NO_2$, etc.) or an electron donating group (e.g., MeO, Me, etc.).

In some embodiments, derivatives, substituents, and functional groups are selected from any suitable organic substitutents comprising carbon, hydrogen, nitrogen, oxygen, sulfur phosphorus, and halogens (e.g., chlorine, fluorine, iodine, etc.). In some embodiments, derivatives, substituents, and functional groups are selected from, but not limited to: alkanes, alkenes, alkynes, cycloalkanes, aromatic groups (e.g. phenyl group, benzyl group, etc.), haloalkanes, alcohols, ketones, aldehydes, acyl halids, carbonates, carboxylates, carboxylic acids, ethers, esters, hydroperoxides, peroxides, amides, amines, imines, imides, azides, diimides, cyanates, nitrates, nitros, nitrosos, pyridines, thiols, sulfides, disulfides, sulfoxides, sulfones, sulfinic acids, sulfonic acids, thiocyantes, thiones, thials, phosphines, phosphonic acids, phosphates, phosphodiesters, and combinations thereof.

In some embodiments, antagonists comprise a molecular structure according to the formula:

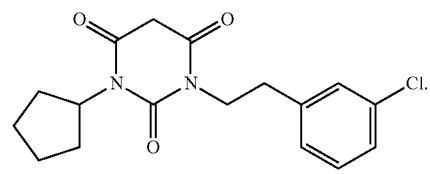 [SMILES: O=C1CC(=O)N(C2CCCC2)C(=O)N1CCc1cccc(Cl)c1]

In some embodiments, antagonists comprise a molecular structure according to the formula:

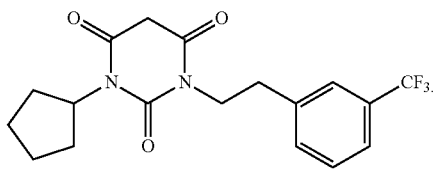 [SMILES: O=C1CC(=O)N(C2CCCC2)C(=O)N1CCc1cccc(C(F)(F)F)c1]

In some embodiments, antagonists comprise a molecular structure according to the formula:

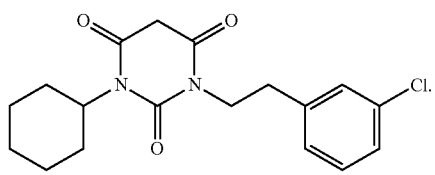 [SMILES: O=C1CC(=O)N(C2CCCCC2)C(=O)N1CCc1cccc(Cl)c1]

In some embodiments, antagonists comprise a molecular structure according to the formula:

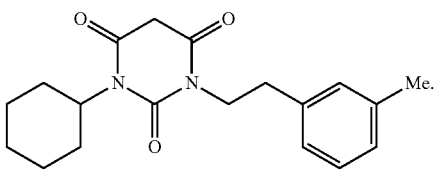 [SMILES: Cc1cccc(CCN2C(=O)CC(=O)N(C3CCCCC3)C2=O)c1]

In some embodiments, antagonists comprise a molecular structure according to the formula:

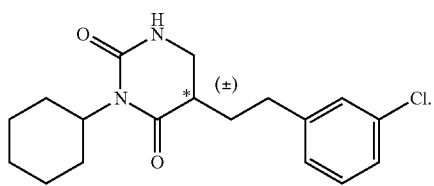 [SMILES: O=C1NCC(CCc2cccc(Cl)c2)C(=O)N1C1CCCCC1]

In some embodiments, antagonists comprise a molecular structure according to the formula:

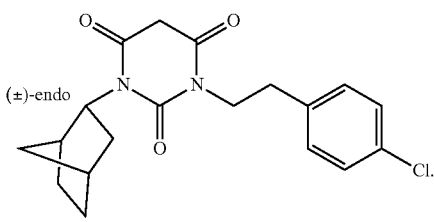 [SMILES: O=C1CC(=O)N(C2CC3CCC2C3)C(=O)N1CCc1ccc(Cl)cc1]

In some embodiments, antagonists comprise a molecular structure according to the formula:

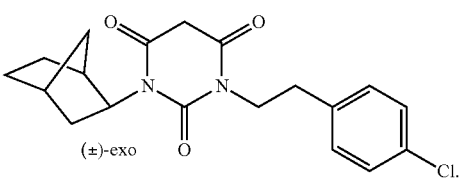 [SMILES: O=C1CC(=O)N(C2CC3CCC2C3)C(=O)N1CCc1ccc(Cl)cc1]

In some embodiments, the present invention provides any of the compounds described in WO/2010129665 (herein incorporated by reference in its entirety) for the treatment, prevention, or symptom reduction of Parkinson's disease, and/or as selective antagonists of Cav1.3.

In some embodiments, the present invention provides compositions and methods for the treatment and/or prevention of one or more neurodegenerative disorders, including, but not limited to: Alexander disease, Alper's disease, Alzheimer's disease, Amyotrophic lateral sclerosis, Ataxia Telangiectasia, Canavan disease, Cockayne syndrome, Corticobasal Degeneration, Creutzfeldt-Jakob disease, Huntington's disease, Kennedy's disease, Krabbe disease, Lewy body dementia, Machado-Joseph disease, Multiple sclerosis, Parkinson's disease, Pelizaeus-Merzbacher Disease, Pick's disease, Primary lateral sclerosis, Refsum's disease, Sandhoff disease, Schilder's disease, Steele-Richardson-Olszewski disease, and Tabes *dorsalis*.

In some embodiments, the invention provides a method comprising steps of administering to a subject suffering from or susceptible to PD (or another neurodegenerative disorder) an effective amount of a provided PYT compound, such that the severity or incidence of one or more symptoms of PD (or another neurodegenerative disorder) is reduced, or its onset is delayed. In some embodiments, a provided PYT compound is administered in the form of a salt or pharmaceutically acceptable composition thereof. In certain embodiments, a provided PYT compound is administered in accordance with the present invention to subjects suffering from or susceptible to a neurodegenerative disease, disorder, or condition in a form or composition and/or according to a regimen useful in the treatment of PD (or another neurodegenerative disorder). In certain embodiments, the subject suffering from or susceptible to PD (or another neurodegenerative disorder) is a human from about 40 to about 85 years of age.

In some embodiments, the present invention provides compositions and methods for prevention, treatment and/or symptom reduction of Parkinson's disease. In some embodiments, the present invention provides selective antagonists of Cav1.3. In some embodiments, compositions of the present invention target SNc DA neurons. In some embodiments, compositions of the present invention inhibit opening of Cav1.3 channels. In some embodiments, administration of compositions of the present invention to subjects (e.g. suffering from PD, at risk for PD) results in decreased calcium flow into SNc DA neurons. In some embodiments, administration of compositions of the present invention to subjects (e.g. suffering from PD, at risk for PD) results in decreased oxidative damage to SNc DA neurons. In some embodiments, administration of compositions of the present invention to subjects (e.g. suffering from PD, at risk for PD) results in reduced risk of developing PD, reduced PD symptoms, treatment of PD, and/or prevention of PD.

In some embodiments, the present invention provides compositions and methods for prevention, treatment and/or symptom reduction of neurodegenerative disorders (e.g. PD). All embodiments of the invention described herein can be applied to the above conditions, diseases, and/or disorders listed herein. When used for the above purposes, said pharmaceutical compound may be administered via any desired oral, parenateral, topical, intervenous, transmucosal, and/or inhalation routes. The pharmaceutical compound may be administered in the form of a composition which is formulated with a pharmaceutically acceptable carrier and optional excipients, flavors, adjuvants, etc. in accordance with good pharmaceutical practice.

In some embodiments of the present invention, compositions are administered to a patient alone or in combination with other therapies, pharmaceuticals, supplements, and/or a specified diet, or in pharmaceutical compositions where it is mixed with excipient(s) or other pharmaceutically acceptable carriers. In some embodiments of the present invention, the pharmaceutically acceptable carrier is pharmaceutically inert. In other embodiments of the present invention, compositions may be administered alone.

Depending on the goal of administration (e.g. type and severity of condition, duration of treatment, etc.), compositions (e.g. comprising Cav1.3-selective antagonists) may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

In some embodiments, compositions (e.g. comprising Cav1.3-selective antagonists) may be in the form of a solid, semi-solid or liquid dosage form: such as tablet, capsule, pill, powder, suppository, solution, elixir, syrup, suspension, cream, lozenge, paste and spray containing the first and second agents formulated appropriately to provide the desired time-release profile. As those skilled in the art would recognize, depending on the chosen route of administration, the composition form is selected.

In some embodiments, the pharmaceutical compound may be administered in single or multiple doses. The particular route of administration and the dosage regimen will be determined by one of skill, in keeping with the condition of the individual to be treated and said individual's response to the treatment. The present invention also provides pharmaceutical compositions in a unit dosage form for administration to a subject, comprising pharmaceutical compounds (e.g. comprising Cav1.3-selective antagonists) and one or more nontoxic pharmaceutically acceptable carriers, adjuvants or vehicles. The amount of the active ingredients (e.g. comprising Cav1.3-selective antagonists) that may be combined with such materials to produce a single dosage form will vary depending upon various factors, as indicated above. A variety of materials can be used as carriers, adjuvants, and vehicles in the composition of the invention, as available in the pharmaceutical art.

In some embodiments, a PYT compound according to the present invention shows a maximum tolerated dose (e.g., when tested in a model organism such as a mouse) of at least about 50, 60, 70, 80, 90, 100, 110, 120, 130, 140, or 150 mg/kg IP. In some embodiments, a PYT compound according to the present invention shows a maximum tolerated dose of greater than about 150 mg/kg IP. In certain embodiments, a PYT compound according to the present invention shows a maximum tolerated dose of at least about 100 mg/kg IP.

In some embodiments, a PYT compound according to the present invention has a therapeutic index of at least about five. In some embodiments, a PYT compound according to the present invention has a therapeutic index of about 6, 7, 8, 9, 10, 11, 12, 13, 14, 15, 16, 17, 18, 19, or 20. In some embodiments, a PYT compound according to the present invention has a therapeutic index of about 25, 30, 35, 40, 45, or 50.

In some embodiments, a PYT compound according to the present invention is characterized by excellent oral availability. In some embodiments, a PYT compound according to the present invention shows about 70%, 80, or 90% oral availability. In some embodiments, a PYT compound according to the present invention shows about 91%, 92%, 93%, 94%, 95%, 96%, 97%, 98%, or 99% oral availability. In certain embodiments, a PYT compound according to the present invention shows about 100% oral availability.

In some embodiments, a PYT compound according to the present invention is characterized by a metabolic half life of about 24 h. In some embodiments, a PYT compound according to the present invention is characterized by a metabolic half life of less than about 24 hours. In some embodiments, a PYT compound according to the present invention is characterized by a metabolic half life of about 12 h. In some embodiments, a PYT compound according to the present invention is characterized by a metabolic half life of about 10 h. In some embodiments, a PYT compound according to the present invention is characterized by a metabolic half life of about 8 h. In some embodiments, a PYT compound according to the present invention is characterized by a metabolic half life of about 2, 3, 4, 5, 6, 7, 8, 9, 10, 11, or 12 h. In some embodiments, a PYT compound according to the present invention is characterized by a metabolic half life of about 20, 30, 40, 50, 60, 70, 80, 90, or 100 minutes. In some embodiments, a PYT compound according to the present invention is characterized by a metabolic half life of at least about 45 minutes.

In some embodiments, a PYT compound according to the present invention shows good blood brain barrier penetration in that a blood:brain concentration ratio of at least about 10:1 is observed. In some embodiments, a PYT compound according to the present invention shows a blood brain barrier penetration in that a blood:brain concentration ratio of about 9:1, 8:1, 7:1, 6:1, 5:1, 4:1, 3:1, 2:1, or 1:1 is observed. In certain embodiments, a blood:brain concentration ratio of about 3:1 is observed.

In some embodiments, a PYT compound according to the present invention is characterized by good tissue penetration such that intraperitoneal administration of 50 mg/kg achieves blood concentrations in the range of about 100, 125, 150, 175 or 200 µM, and/or brain concentrations in the range of 30, 40, 50, 60, or 70 µM (e.g., in a model organism such as a mouse). In some embodiments, intraperitoneal administration of about 60 mg/kg achieves a blood concentration of about 150 micromolar, and/or a brain concentration of about 50 micromolar. In some embodiments, intraperitoneal administration of about 50 mg/kg achieves a blood concentration of about 150 micromolar, and/or a brain concentration of about 50 micromolar. In some embodiments, intraperitoneal administration of about 40 mg/kg achieves a blood concentration of about 150 micromolar, and a brain concentration of about 50 micromolar. In some embodiments, intraperitoneal administration of less than about 40 mg/kg achieves a blood concentration of about 150 micromolar, and/or a brain concentration of about 50 micromolar. In some embodiments, intraperitoneal administration of about 10, 20, 30, 40, 50, 60, 70, 80, 90, or 100 mg/kg achieves a blood concentration of about 150 micromolar, and/or a brain concentration of about 50 micromolar.

In some embodiments, a PYT compound according to the present invention is characterized by good tissue penetration such that oral administration of 50 mg/kg achieves blood concentrations in the range of about 100, 125, 150, 175 or 200 micromolar, and/or brain concentrations in the range of 30, 40, 50, 60, or 70 micromolar (e.g., in a model organism such as a mouse). In some embodiments, oral administration of about 60 mg/kg achieves a blood concentration of about 150 micromolar, and/or a brain concentration of about 50 micromolar. In some embodiments, oral administration of about 50 mg/kg achieves a blood concentration of about 150 micromolar, and/or a brain concentration of about 50 micromolar. In some embodiments, oral administration of about 40 mg/kg achieves a blood concentration of about 150 micromolar, and a brain concentration of about 50 micromolar. In some embodiments, oral administration of less than about 40 mg/kg achieves a blood concentration of about 150 micromolar, and/or a brain concentration of about 50 micromolar. In some embodiments, oral administration of about 10, 20, 30, 40, 50, 60, 70, 80, 90, or 100 mg/kg achieves a blood concentration of about 150 micromolar, and/or a brain concentration of about 50 micromolar.

In some embodiments, a PYT compound according to the present invention exhibits $EC_{50}$ values of less than about 30 µM. In some embodiments, a PYT compound according to the present invention exhibits $EC_{50}$ values of less than about 20 µM. In some embodiments, a PYT compound according to the present invention exhibits $EC_{50}$ values of less than about 10 µM. In some embodiments, a PYT compound according to the present invention exhibits $EC_{50}$ values of about 9, 8, 7, 6, 5, 4, 3, 2, or 1 µM. In certain embodiments, a PYT compound according to the present invention exhibits $EC_{50}$ values of less than about 1 µM. In certain embodiments, a PYT compound according to the present invention exhibits $EC_{50}$ values between 0.5 and 5.0 µM. In certain embodiments, a PYT compound according to the present invention exhibits an $EC_{50}$ value of about 2 µM.

In some embodiments, a subject is administered 1-10 mg, 109-20 mg, 20-30 mg, 40-50 mg, or 60-70 mg per day of the compounds of the present invention.

In some embodiments, compositions of the present invention are co-administered with other therapeutics for treatment or prevention of PD or other neurodegenerative diseases or disorders. In some embodiments, PYT compounds are co-administered with any suitable agents (e.g., therapeutics, nutriceuticals, pharmaceuticals, etc.), for treatment of PD, prevention of PD, symptom reduction, easing side effects of treatments, deducing drug interactions, etc.

EXPERIMENTAL

The following examples are provided in order to demonstrate and further illustrate certain preferred embodiments and aspects of the present invention and are not to be construed as limiting the scope thereof.

Example 1

Experiments were conducted during development of embodiments of the present invention using the high-throughput screening (HTS) facility of Northwestern University, to screen ~30,000 commercial compounds using a fluorescence imaging plate reader (FLIPR) system. No Cav1.3-selective compounds were identified in this library.

Figure 2:
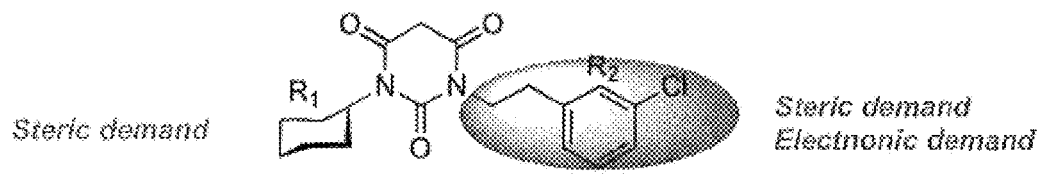
FIG. 2 shows a schematic of exemplary PYT library design considerations.

Further experiments were conducted to screen for Cav1.3-selective antagonists in a library of ~300 synthetic compounds, and the pyrimidine-2,4,6-triones (PYT) as a scaffold that selectively antagonizes the Cav1.3 L-type calcium channels. PYT molecules were further investigated by synthesizing ~150 new analogues of the PYT scaffold with the general structure shown in FIG. 1. Analogues were designed to probe several different structural features of PYT: substitution on the alkyl R1, substitution on the aryl ring R2, and modification of the PYT skeleton (SEE FIG. 2). To probe the electronic and steric demands on the aryl ring of R2, electron-withdrawing substituents (F, Cl, Br, $CF_3$, $CO_2H$, CN, $NO_2$) and electron-donating substituents (MeO, Me) were chosen. To probe the required distance between the pyrimidinetrione ring and the aryl ring of R2, four different alkyl chains $((CH_2)_n$, wherein n=1-4) were placed between the rings. To probe the steric demands on R1, cycloalkyl substituents (cycloheptyl, cyclohexyl, cyclopentyl, cyclobutyl, cyclopropyl), bicycloalkyl substituents [(±)-2-endo-norbornyl, (±)-2-exonorbornyl], and tricycloalkyl substituents (1adamantyl, 2-adamantyl) were chosen as R1. Finally, to understand the steric and electronic demands on the skeleton, the PYT ring was switched to a cyanurate, barbiturate, imidazolinetrione, diazepane, pyrimidineone, dihydrouracil, triazole, or hydanton ring.

Figure 3:
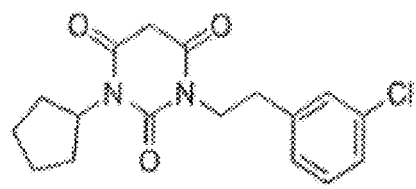
FIG. 3 shows structures of several selective PYT anatagonists identified.
Figure 3:
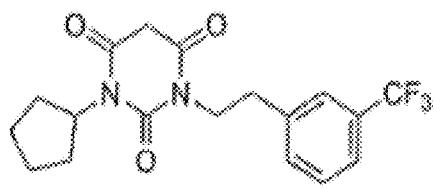
Figure 3:
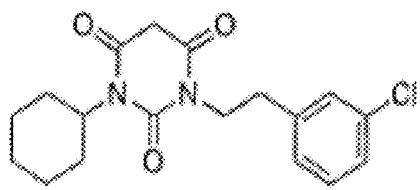
Figure 3:
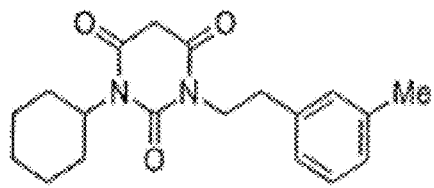
Figure 4:
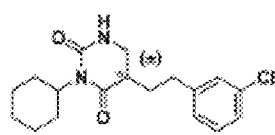
FIG. 4 shows structures of several potent PYT anatagonists identified.
Figure 4:
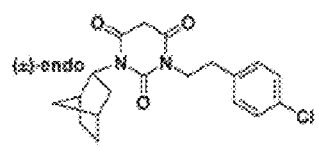
Figure 4:
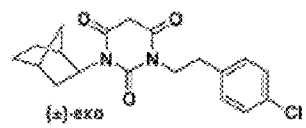

Several PYT molecules have been identified that selectively antagonize Cav1.3 L-type calcium channels. Four members of this Cav1.3 selectivity subgroup (SEE FIG. 3) have antagonistic activity ($IC_{50}$ 1-2 µM) and have more than 100-fold selectivity for the Cav1.3 channel over the Cav1.2 channel, as determined from the ratio of $IC_{50}$ values for the two cell lines. For example, the $IC_{50}$ value for SKP004C08 with Cav1.3 is 1.61 µM and its selectivity over Cav1.2 is greater than 1000-fold (SEE FIG. 3). SKP005C06 and SKP004E02 were also identified as antagonists (SEE FIG. 4). Although the selectivity for Cay1.3 over Cay1.2 is only 4-fold, the $IC_{50}$ value for SKP005C06 with Cav1.3 is 150 nM. For $SKP004CO_2$, the $IC_{50}$ value was 180 nM for Cav1.3, and the selectivity was 44-fold.

Using the same cell lines from the initial screening, whole-cell voltage clamp recordings were made of either Cav1.3 LTCC or Cav1.2 LTCC containing HEK293 cells in the absence or presence of SKP004C08 at 1 µM. Bath application of SKP004C08 blocks ~35% of the Cav1.3 channel current. SKP004C08 at the same concentration had no effect on Cav1.2 channel currents.

With whole-cell patch recordings, important characteristics of this PYT action on Cav1.3 L-type Ca2+ channels have been identified. For example, it has been demonstrated that PYT compounds at 1 µM concentrations are reversible and seem to have greater potency at more depolarized potentials. The same concentration of PYT (1 µM) instead of blocking ~35% of the peak current when held at −70 mV, blocks ~90% of the peak current when held at −50 mV. Both reversibility and voltage dependent block are hallmarks of dihydropyridines (DHPs).

In light of similar biophysical and pharmacological characteristics of DHPs and PYTs, the locus of DHP binding and PYT binding was examined. A single amino acid residue mutation in the Cav1.3 DHP binding site renders the channel ~100 less sensitive to DHP antagonism. This mutation doubled the apparent $IC_{50}$ for PYT compounds, suggesting that there is a similar binding site.

Example 2

Experiments were conducted during development of embodiments of the present invention to develop highly selective Cav1.3 channel antagonists: starting with a HTS of several libraries, SAR based modification, and further whole-cell patch clamp confirmation (Hamill et al. (1981) Pfluegers Arch. European Journal of Physiology 391:85-100.; herein incorporated by reference in its entirety).

HTS (High Throughput Screen) Setup and Identification of Hits.

The biological assay included the preparation of cultures of Cav1.3 and Cav1.2 LTCCs expressed in HEK293 cells. Because Cav1.3 and Cav1.2 cells were used for comparative screens, it was necessary for each of these cells to have the same characteristics in order to compare the results of each compound with the two types of channels. Biologically equivalent Cav1.3 and Cav1.2 cells were initially used, but after a few rounds, where half of each batch of cells was used for screening and the rest was used for culture growth for the next round of screening, it was observed that synchronization of the two cell lines deteriorated. This approach was replaced by a cryopreserved cell method in which a large batch of cells expressing each of the calcium channels was stored frozen, and an aliquot of the same batch was utilized for continuous compound screening. A FLIPR based HTS for Cav1.3 channels was used to screen 60,480 commercial compounds (ADSI set 6,800; ChemBridge diverse/lead like set 20,000; ChemDiv diverse set 30,000; NIH clinical trial set 480, NCI/DTP set 3,200). Compounds selected for this screen were not from focused libraries of ion channel blockers, in order to identify novel antagonists of Cav1.3 channels that do not block other ion channels.

Testing of these commercial compounds for Cav1.3 channels resulted in a hit of a single scaffold, namely thiotriazoles (See, e.g., FIG. 5A); however, these compounds, and a series of analogues were poorly selective for Cav1.3 channels. Subsequently, a few hundred compounds were screened from a compound library originally prepared for other treatment CNS diseases. From that screen, the pyrimidine 2,4,6-trione (PYT) scaffold was identified as a class of weakly selective antagonists for Cav1.3 channels (SEE FIG. 5B). The initial symmetric PYT hits displayed moderate potency and Cav1.3 channel selectivity (8-fold over Cav1.2 channels). Furthermore, the scaffold was of interest because of its favorable pharmacological properties such as, ADME, low toxicity, brain penetration, and oral bioavailability determined previously. (Xia et al. (2010) *J. Med. Chem.* 54: 2409-2421.; herein incorporated by reference in its entirety). In addition, there was great potential to explore structure-activity relationships (SARs).

SAR Based Hit Modification.

About 120 PYT analogues were synthesized to develop a SAR. The general approach taken to N,N-disubstituted PYT synthesis involved the use of the Wöhler urea synthesis (Wöhler F (1828) Annalen der Physik and Chemie. 88:253-256.; herein incorporated by reference in its entirety), the coupling of isocyanate with various amines, and Biltz and Wittek's condensation of ureas with activated malonic acid (See Scheme 1; Biltz & Wittek, H (1921) Chem Ber. 54:1035-1058.; herein incorporated by reference in its entirety). The treatment of malonyl chloride with the ureas provided the condensation products in good yields. Further optimization of each step allowed a one-pot parallel synthesis, and sufficient sample purity was achieved by fractional filtration of the final reaction mixture through a silica gel plug (10 cm). This synthetic route permitted the construction of the majority of PYT library members in sufficient quantities and purity for assay against Cav1.3 and Cav1.2 LTCCs.

Scheme 1. Common synthetic route to the PYT scaffold

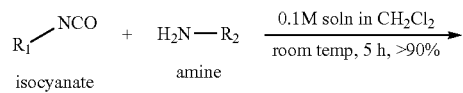

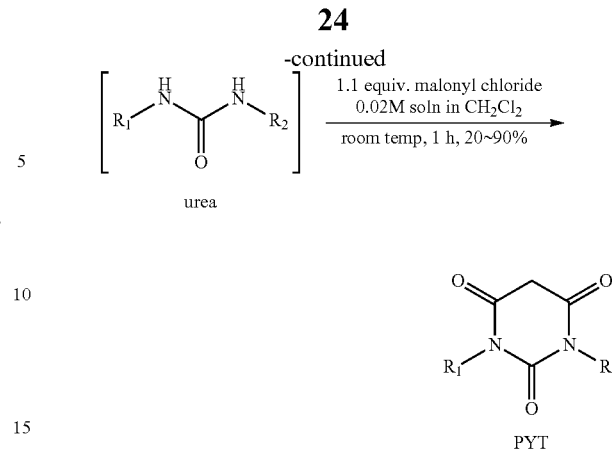

Figure 14:
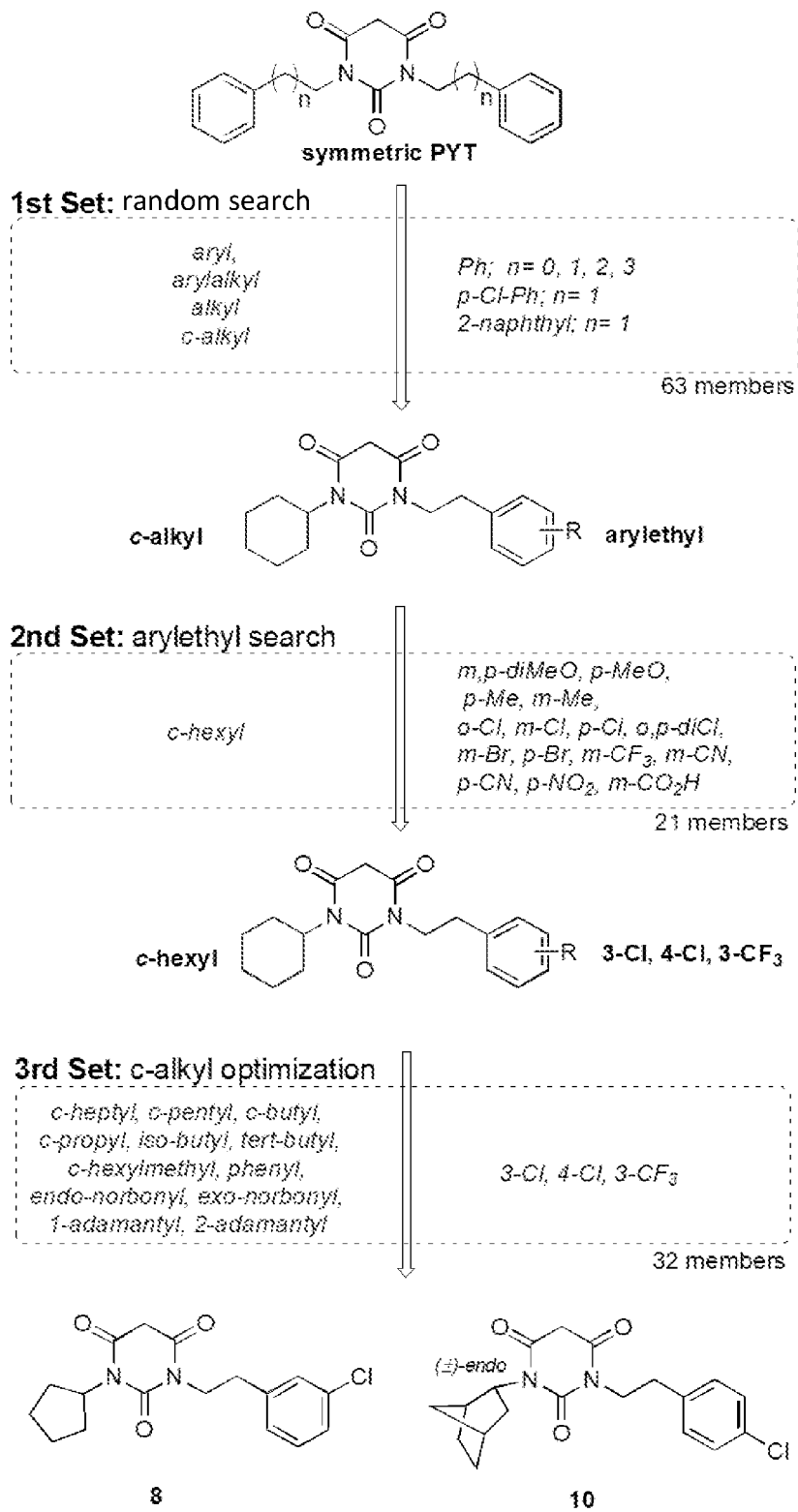
FIG. 14 shows PYT analogue synthesis.

The first library (63 members; See Table 1) of PYTs were synthesized to probe several different structural features based on results from the initial hit PYTs, including substitution on the $R_1/R_2$ side chain and substitution on the aryl ring of $R_1$. Four $R_2$ substituents were used (4-chlorophenethyl, 3-phenylpropyl, 4-phenylbutyl, and 2-naphthylethyl), and the $R_1$ aryl ring was substituted. To probe the electronic effects and steric demands on the $R_1$ aryl ring, electron-withdrawing (F, Cl, Br, $CF_3$, $NO_2$) substituents and methyl were chosen. Because electron rich substituents in the original library did not exhibit good selectivity or potency with Cav1.3 channels, electron rich substituents (except methyl) were not considered at this stage. To probe the required distance between the PYT ring and the aryl ring of $R_1$, four different alkyl chains ($C_1$-$C_4$) were incorporated into the sidechain. To probe the steric requirements of $R_1$, cyclopentyl, cyclohexyl, 2-phenyl-propyl, indanyl, and tetralinyl substituents were used. From the first library of analogues assayed, three members (1, 2, 3) were shown to inhibit Cav1.3 channels with excellent selectivity (>34-fold from a comparison of the $IC_{50}$ value with Cav1.2 to that with Cav1.3) compared to that of the initial hit (Table 4 and FIG. 14). This is the first class of Cav1.3-selective antagonists; the bulky $R_1$ cycloalkyl group may be involved in specific steric interactions with neighboring residues in the Cav1.2 channel binding site causing weak binding.

TABLE 1

Cav1.3 and Cav1.2 Inhibition Data for the first library

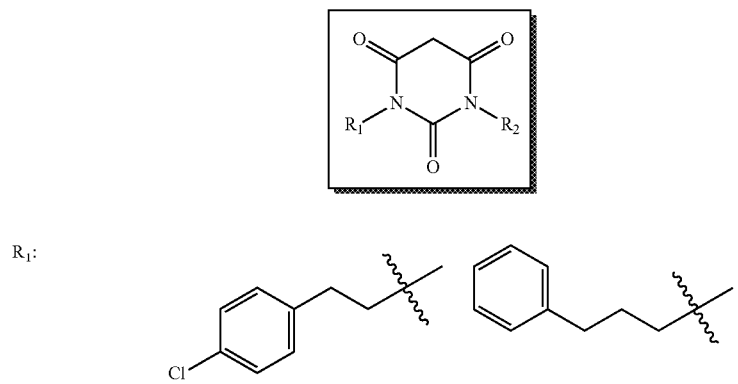

TABLE 1-continued
Cav1.3 and Cav1.2 Inhibition Data for the first library
R$_2$:
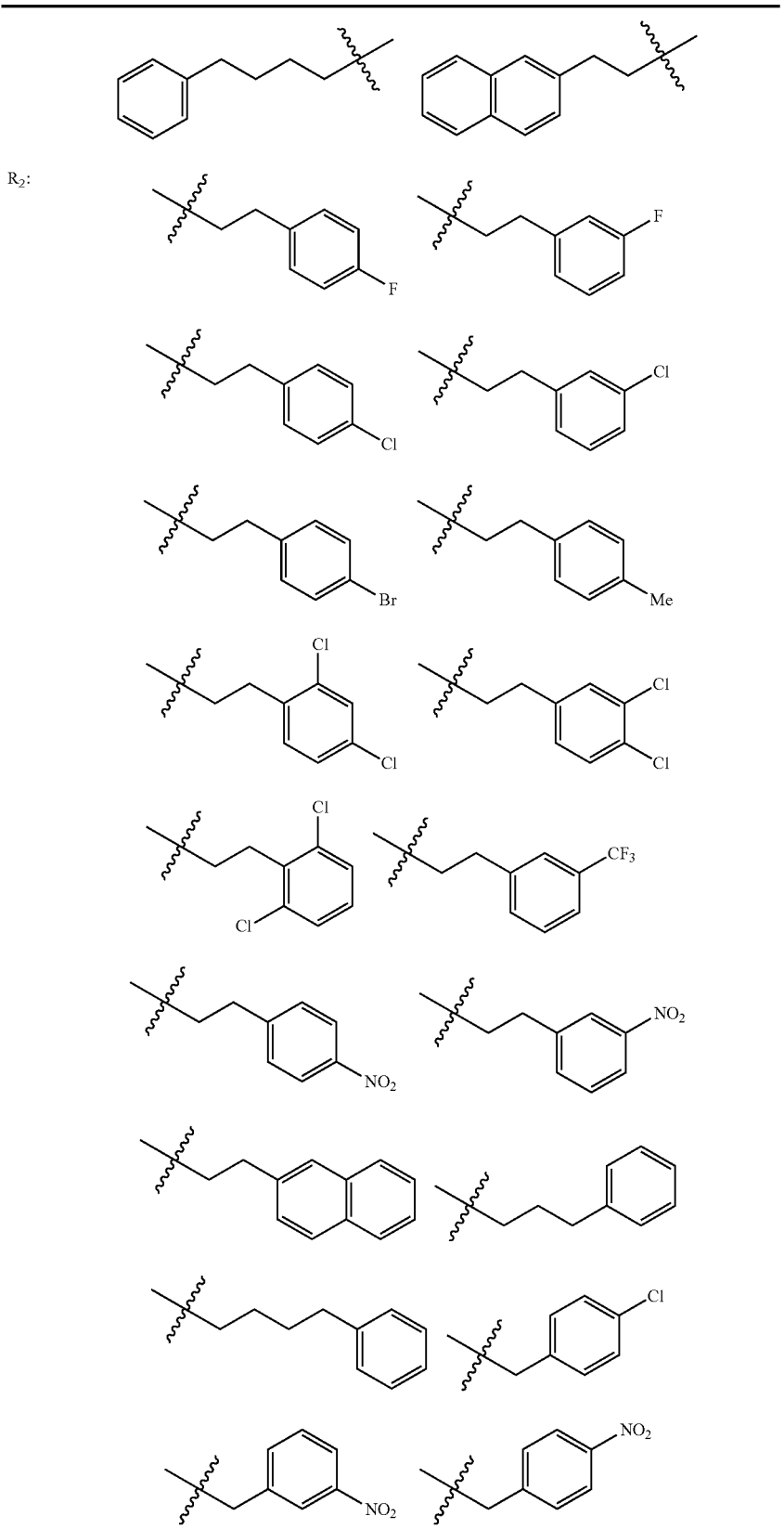

TABLE 1-continued

Cav1.3 and Cav1.2 Inhibition Data for the first library

|   |   | IC$_{50}$ (μM) | | |
|---|---|---|---|---|
| # | R1 | R2 | Cav1.3 | Cav1.2 | Selectivity |
| 11 | 4-Cl-phenethyl | 4-Cl-phenethyl | 1.8 (±0.4) | 2.1 (±0.5) | 1.2 |
| 12 | 4-Cl-phenethyl | 3-Cl-phenethyl | 1.9 (±0.5) | 4.4 (±0.1) | 2.3 |
| 13 | 4-Cl-phenethyl | 2,4-Cl$_2$-phenethyl | 1.8 (±0.2) | 2.8 (±0.8) | 1.5 |
| 14 | 4-Cl-phenethyl | 3,4-Cl$_2$-phenethyl | 1.9 (±0.5) | 1.3 (±0.4) | 0.7 |
| 15 | 4-Cl-phenethyl | 2,6-Cl$_2$-phenethyl | 2.7 (±0.4) | 1.9 (±0.5) | 0.7 |
| 16 | 4-Cl-phenethyl | 4-Br-phenethyl | 1.6 (±0.3) | 2.1 (±0.6) | 1.3 |
| 17 | 4-Cl-phenethyl | 4-Me-phenethyl | 1.1 (±0.6) | 7.1 (±1.6) | 6.7 |
| 18 | 4-Cl-phenethyl | 4-F-phenethyl | 1.1 (±0.3) | 3.3 (±1.1) | 3.1 |
| 19 | 4-Cl-phenethyl | 3-F-phenethyl | 1.9 (±0.5) | 2.8 (±0.5) | 1.5 |
| 20 | 4-Cl-phenethyl | 3-CF$_3$-phenethyl | 0.4 (±0.1) | 2.8 (±1.4) | 6.2 |
| 21 | 4-Cl-phenethyl | 2-phenylpropyl | 1.3 (±0.2) | 6.2 (±0.7) | 5.0 |
| 22 | 4-Cl-phenethyl | 3-NO$_2$-benzyl | 21.2 (±2.5) | 9.5 (±2.8) | 0.4 |
| 23 | 4-Cl-phenethyl | 4-NO$_2$-phenethyl | 3.4 (±0.6) | 2.7 (±0.6) | 0.8 |
| 24 | 4-Cl-phenethyl | 3-NO$_2$-phenethyl | 2.7 (±0.8) | 2.6 (±0.4) | 1.0 |
| 25 | 4-Cl-phenethyl | 4-Cl-Benzyl | 2.1 (±0.5) | 1.9 (±0.1) | 0.9 |
| 26 | 4-Cl-phenethyl | 4-Phenylbutyl | 0.9 (±0.1) | 0.8 (±0.3) | 0.9 |
| 27 | 4-Cl-phenethyl | 3-Phenylpropyl | 1.1 (±0.3) | 2.1 (±0.6) | 1.9 |
| 28 | 4-Cl-phenethyl | Octyl | 1.5 (±0.3) | 2.8 (±1.5) | 1.9 |
| 1 | 4-Cl-phenethyl | Cyclohexyl | 1.1 (±0.8) | 38.8 (±4.0) | 35.1 |
| 29 | 4-Cl-phenethyl | Cyclopentyl | 1.4 (±0.3) | 22.4 (±3.0) | 16.4 |
| 30 | 4-Cl-phenethyl | 1-Tetralinyl | 5.6 (±2.6) | 12.8 (±8.5) | 2.3 |
| 31 | 4-Cl-phenethyl | 2-Indanyl | 1.3 (±0.2) | 3.0 (±1.5) | 2.2 |
| 32 | 4-Cl-phenethyl | 1-Indanyl | 8.4 (±2.0) | 14.5 (±8.2) | 1.7 |
| 33 | 4-Cl-phenethyl | 2-(2-Naphthyl)ethyl | 1.1 (±0.4) | 1.4 (±0.6) | 1.2 |
| 34 | 4-Cl-phenethyl | GlyOMe | 108.1 (±25.6) | — | — |
| 35 | 4-Cl-phenethyl | L-AlaOMe | 77.7 (±11.1) | 88.2 (±26.2) | 1.1 |
| 36 | 4-Cl-phenethyl | L-LeuOMe | 20.6 (±4.8) | 17.1 (±10.7) | 0.8 |
| 37 | 4-Cl-phenethyl | L-PheOAllyl | 9.4 (±4.0) | 9.1 (±5.0) | 1.0 |
| 38 | 4-Phenylbutyl | 3-Cl-phenethyl | 1.3 (±0.7) | 6.2 (±5.0) | 4.9 |
| 39 | 4-Phenylbutyl | 3,4-Cl2-phenethyl | 1.3 (±0.6) | 3.1 (±2.2) | 2.3 |
| 40 | 4-Phenylbutyl | 4-Br-phenethyl | 1.1 (±0.2) | 2.0 (±1.0) | 1.9 |
| 41 | 4-Phenylbutyl | 4-Me-phenethyl | 1.1 (±0.5) | 15.5 (±14.3) | 14.1 |
| 42 | 4-Phenylbutyl | 3-F-phenethyl | 1.6 (±0.5) | 5.3 (±3.1) | 3.3 |
| 43 | 4-Phenylbutyl | 3-CF$_3$-phenethyl | 0.5 (±0.1) | 1.1 (±0.7) | 2.3 |
| 44 | 4-Phenylbutyl | 2-phenylpropyl | 2.1 (±0.8) | 15.8 (±4.5) | 7.7 |
| 45 | 4-Phenylbutyl | 4-NO$_2$-Benzyl | 7.7 (±1.7) | 4.4 (±2.5) | 0.6 |
| 46 | 4-Phenylbutyl | 4-NO$_2$-phenethyl | 3.5 (±0.8) | 4.1 (±2.2) | 1.2 |
| 47 | 4-Phenylbutyl | 3-NO$_2$-phenethyl | 3.0 (±0.7) | 3.0 (±2.2) | 1.0 |
| 48 | 4-Phenylbutyl | 4-Cl-Benzyl | 2.1 (±0.6) | 7.7 (±4.4) | 3.7 |
| 49 | 4-Phenylbutyl | 3-Phenylpropyl | 1.3 (±0.5) | 2.6 (±1.2) | 2.0 |
| 2 | 4-Phenylbutyl | Cyclopentyl | 1.3 (±0.5) | 43.8 (±8.2) | 33.7 |
| 50 | 4-Phenylbutyl | 1-Tetralinyl | 36.5 (±15.2) | 34.1 (±28.5) | 0.9 |
| 51 | 4-Phenylbutyl | 2-Indanyl | 3.3 (±0.3) | 4.9 (±3) | 1.5 |
| 52 | 4-Phenylbutyl | 1-Indanyl | 5.3 (±0.5) | 5.7 (±4.4) | 1.1 |
| 53 | 4-Phenylbutyl | 2-(2-Naphthyl)ethyl | 1.9 (±0.6) | 2.5 (±0.8) | 1.3 |
| 3 | 3-Cl-phenethyl | Cyclohexyl | 1.4 (±0.4) | 53.1 (±4.5) | 38.0 |
| 54 | 3-Phenylpropyl | 3,4-Cl$_2$-phenethyl | 4.3 (±1.1) | 6.9 (±2.5) | 1.6 |
| 55 | 3-Phenylpropyl | 4-F-phenethyl | 1.3 (±0.4) | 2.2 (±0.1) | 1.7 |
| 56 | 3-Phenylpropyl | 3-F-phenethyl | 1.6 (±0.5) | 2.5 (±0.6) | 1.5 |
| 57 | 3-Phenylpropyl | 3NO$_2$-Benzyl | 16.5 (±2.4) | 13.0 (±3.1) | 0.8 |
| 58 | 3-Phenylpropyl | 3-NO$_2$-phenethyl | 10.4 (±2.6) | 9.5 (±2.9) | 0.9 |
| 59 | 3-Phenylpropyl | 4-Cl-Benzyl | 21.9 (±3.6) | 26.0 (±1.6) | 1.2 |
| 60 | 3-Phenylpropyl | Octyl | 1.1 (±0.2) | 2.6 (±0.1) | 2.5 |
| 61 | 3-Phenylpropyl | 2-(2-Naphthyl)ethyl | 1.0 (±0.3) | 1.2 (±0.4) | 1.3 |
| 62 | 2-(2-Naphthyl)ethyl | 2-(2-Naphthyl)ethyl | 2.9 (±0.5) | 1.8 (±0.3) | 0.6 |
| 63 | 2-(2-Naphthyl)ethyl | 3,4-Cl$_2$-phenethyl | 4.0 (±0.5) | 3.8 (±0.3) | 1.0 |
| 64 | 2-(2-Naphthyl)ethyl | 4-F-phenethyl | 1.8 (±0.3) | 3.8 (±0.9) | 2.1 |

TABLE 1-continued

Cav1.3 and Cav1.2 Inhibition Data for the first library

| | | | | | |
|---|---|---|---|---|---|
| 65 | 2-(2-Naphthyl)ethyl | 3-NO$_2$-benzyl | 4.8 (±1.3) | 5.0 (±0.7) | 1.0 |
| 66 | 2-(2-Naphthyl)ethyl | 4-Cl-benzyl | 1.7 (±0.8) | 2.4 (±0.2) | 1.4 |
| 67 | 2-(2-Naphthyl)ethyl | Octyl | 1.9 (±0.7) | 8.9 (±3.7) | 4.8 |
| 68 | Cyclohexyl | 4-F-phenethyl | 9.4 (±1.5) | 166 | 17.7 |
| 69 | Methyl | 3-NO$_2$-benzyl | — | 167 | — |
| 70 | 3-NO$_2$-Phenethyl | 3-NO$_2$-phenethyl | — | 173 | — |

The second library (21 members; Table 2) was prepared to probe the electronic and steric demands on the aryl ring R$_2$, with a cyclohexyl group (R$_1$). Electron-withdrawing substituents (F, Cl, Br, CF$_3$, CO$_2$H, CN, NO$_2$) and electron-donating substituents (MeO, Me) were used for R$_2$. When R$_1$ was cyclohexyl, the analogues with R$_2$ m-chlorophenethyl (3), m-methylphenethyl (4), m-bromophenethyl (5), and m-trifluoromethylphenethyl (6) were the most selective antagonists for Cav1.3 channels (Table 4 and FIG. 14). The selectivity of the meta-substituted analogues results from the loss of binding affinity for Cav1.2 channels. This meta-substitution effect also prevailed when utilizing cyclopentyl as the R$_1$ substituent, encompassing the third library. However, hydrophilic functional groups on the arylalkyl R$_2$ somehow diminished the binding affinity for both calcium channels; —CO$_2$H, —NO$_2$, —CN, or —OMe substituted arylalkyl members mostly displayed IC$_{50}$ values >9 μM for both Cav1.3 and Cav1.2 LTCCs.

TABLE 2

Cav1.3 and Cav1.2 Inhibition Data for the second library

TABLE 2-continued

Cav1.3 and Cav1.2 Inhibition Data for the second library

| | | | IC50 (µM) | | |
|---|---|---|---|---|---|
| Name | R1 | R2 | Cav1.3 | Cav1.2 | Selectivity |
| 71 | Cyclohexyl | 3,4-(MeO)$_2$-phenethyl | 32.5 (±8.8) | 75.5 (±16.4) | 2.3 |
| 72 | Cyclohexyl | 4-MeO-phenethyl | 9.4 (±3.2) | 26.2 (±1.8) | 2.8 |
| 73 | Cyclohexyl | 2-Thiopenyl-ethyl | 11.4 (±1.3) | 37.2 (±8.6) | 3.3 |
| 74 | Cyclohexyl | 4-Me-phenethyl | 1.8 (±0.6) | 6.1 (±5.5) | 3.4 |
| 4 | Cyclohexyl | 3-Me-phenethyl | 2.2 (±0.9) | 77.1 (±48.7) | 35.4 |
| 75 | Cyclohexyl | 2,4-Cl$_2$-phenethyl | 1.5 (±0.5) | 40.3 (±3.6) | 27.0 |
| 76 | Cyclohexyl | 2-Cl-phenethyl | 5.2 (±2.2) | 44.5 (±25.8) | 7.7 |
| 77 | Cyclohexyl | 4-Br-phenethyl | 0.8 (±0.3) | 21.3 (±1.9) | 26.4 |
| 5 | Cyclohexyl | 3-Br-phenethyl | 1.3 (±0.4) | 45.8 (±12.7) | 34.0 |
| 6 | Cyclohexyl | 3-CF$_3$-phenethyl | 1.3 (±0.1) | 25.8 (±8.5) | 20.3 |
| 78 | Cyclohexyl | 4-CN-phenethyl | 49.8 (±8.9) | 56 (±10.4) | 1.1 |
| 79 | Cyclohexyl | 3-CN-phenethyl | 10.5 (±3.6) | 36.5 (±11.9) | 3.5 |
| 80 | Cyclohexyl | 4-NO$_2$-phenethyl | 8.9 (±2.6) | 10.5 (±0.8) | 1.2 |
| 81 | Cyclohexyl | 4-MeO-benzyl | 32.2 (±9.9) | 67.8 (±12.7) | 2.1 |
| 82 | Cyclohexyl | 4-Cl-benzyl | 8.1 (±2.4) | 119.1 (±64) | 14.7 |
| 83 | Cyclohexyl | 3-NO$_2$-benzyl | 48.2 (±3.1) | 59.5 (±17.1) | 1.2 |
| 84 | Cyclohexyl | 3-Phenylpropyl | 6.3 (±1.4) | 30.5 (±10) | 4.9 |
| 85 | Cyclohexyl | 1-Indanyl | 16.4 (±6.2) | 19.2 (±2.9) | 1.2 |
| 86 | Cyclohexyl | 1-(4-Cl-phenyl)-propyl-2- | 2.1 (±0.6) | 16.8 (±6.9) | 7.9 |
| 87 | Cyclohexyl | 2-(4-Cl-phenyl)-propyl-1- | 1.5 (±0.5) | 52.9 (±16.5) | 34.6 |
| 88 | Cyclohexyl | 2-Phenoxyethyl | 9.5 (±2.9) | 11.8 (±3.6) | 1.2 |
| 89 | Cyclohexyl | 3-CO$_2$H-phenethyl | 73.0 (±16.7) | 64.7 (±11.1) | 0.9 |

Figure 6:
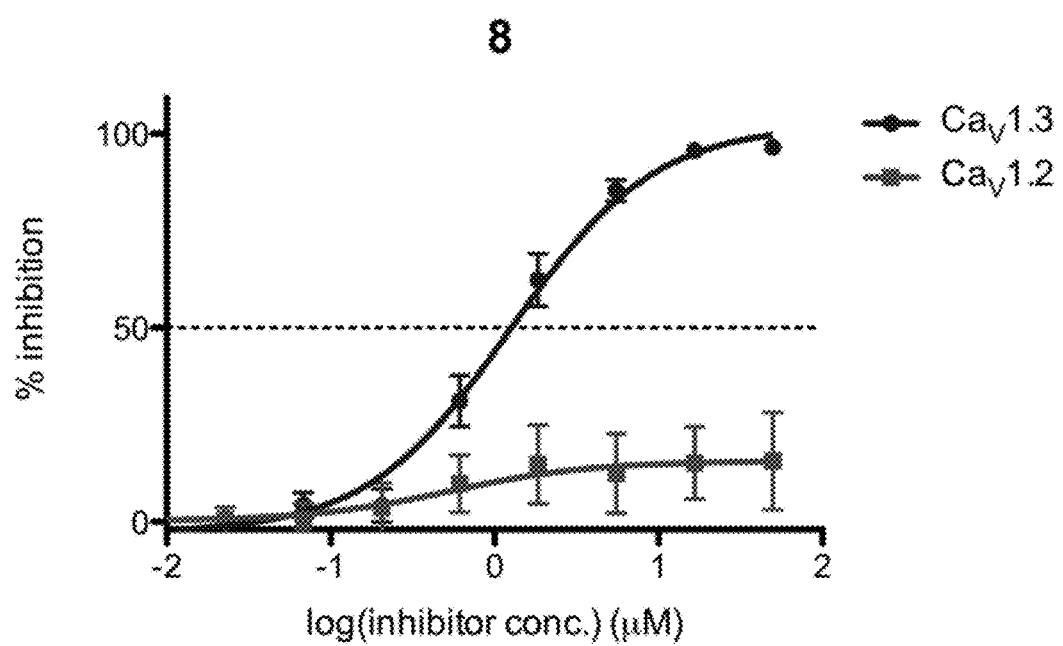
FIG. 6 shows a FLIPR assay dose-response curve for Cav1.3 channels and Cav1.2 channels with compound 8.

The third library (32 members; Table 3) was prepared to probe the steric demands on R$_1$, while maintaining the three best side chains (m-chlorophenethyl, p-chlorophenethyl, m-trifluoromethylphenylethyl) of previous libraries as R$_2$. Cycloalkyl substituents (cycloheptyl, cyclohexyl, cyclopentyl, cyclobutyl, cyclopropyl), bicycloalkyl substituents [(±)-2-endo-norbornyl, (±)-2-exo-norbornyl], tricycloalkyl substituents (1-adamantyl, 2-adamantyl), and miscellaneous bulky substituents were used for R$_1$. The trend that emerged from this library was a steric effect of the lipophilic side chain of R$_1$. Among the various cycloalkyl chains of R$_1$, the cyclopentyl derivatives (7 and 8) were the most highly selective antagonists for the Cav1.3 channels (Table 4 and FIG. 14); 8 (N-(3-chlorophenethyl)-N'-cyclopentyl-pyrimidine-2,4,6-(1H,3H,5H)-trione) is the most selective Cav1.3 antagonist, having 1000-fold selectivity for Cav1.3 over Cav1.2 channels (from the ratio of IC$_{50}$ values for Cav1.2 and Cav1.3) with an IC$_{50}$ of 1.7 µM (SEE FIG. 6). Compounds 9 and 10 are the most potent antagonists of this series of molecules (800 nM and 600 nM, respectively) and have moderate selectivity (about 25-fold).

TABLE 3

Cav1.3 and Cav1.2 Inhibition Data for the third library

| | | | IC50 (μM) | | |
|---|---|---|---|---|---|
| Name | R1 | R2 | Cav1.3 | Cav1.2 | Selectivity |
| 90 | Cycloheptyl | 3-CF₃-phenethyl | 1.7 (±0.3) | 5.7 (±1.7) | 3.4 |
| 91 | Cycloheptyl | 3-Cl-phenethyl | 2.5 (±0.3) | 45.6 (±12.9) | 18.5 |
| 92 | Cycloheptyl | 4-Cl-phenethyl | 2.2 (±0.5) | 32.8 (±2.5) | 15.0 |
| 93 | Cycloheptyl | 3-Me-phenethyl | 13.2 (±1.9) | 30.7 (±9.1) | 2.3 |
| 94 | Cycloheptyl | 4-Me-phenethyl | 0.9 (±0.3) | 14.9 (±4.3) | 16.0 |
| 7 | Cyclopentyl | 3-CF₃-phenethyl | 1.1 (±0.2) | 325.7 (±217.7) | 305.4 |
| 8 | Cyclopentyl | 3-Cl-phenethyl | 1.7 (±0.2) | 1730 (±467.6) | 1008.2 |
| 95 | Cyclopentyl | (±)-1-Phenyl-propyl-2- | 0.7 (±0.2) | 16.0 (±16.2) | 23.0 |
| 96 | Cyclopentyl | (±)-2-Phenyl-propyl-1- | 1.0 (±0.2) | 16.9 (±9.5) | 17.6 |
| 97 | Cyclopentyl | 3-Me-phenethyl | 1.1 (±0.3) | 52.1 (±31) | 49.1 |
| 98 | Cyclopentyl | 4-Me-phenethyl | 1.7 (±0.5) | 35.8 (±17.3) | 20.7 |
| 99 | Cyclobutyl | 3-Cl-phenethyl | 2.7 (±0.6) | 14.6 (±2.4) | 5.4 |
| 100 | Cyclobutyl | 4-Cl-phenethyl | 1.8 (±0.5) | 4.9 (±1.6) | 2.8 |
| 101 | Cyclopropyl | 3-Cl-phenethyl | 26.8 (±2.8) | 5.4 (±0.4) | 0.2 |
| 102 | Cyclopropyl | 4-Cl-phenethyl | 19.6 (±4.2) | 5.0 (±0.9) | 0.3 |
| 103 | 3-F-Phenyl | 3-Cl-phenethyl | 18.6 (±3.9) | 9.7 (±2.9) | 0.5 |
| 104 | 3-F-Phenyl | 4-Cl-phenethyl | — | — | — |
| 105 | t-Butyl | 3-Cl-phenethyl | 10.5 (±4.4) | 7.2 (±2.4) | 0.7 |
| 106 | t-Butyl | 3-CF₃-phenethyl | 1.1 (±0.3) | 6.1 (±3) | 5.7 |
| 107 | s-Butyl | 3-Cl-phenethyl | 1.9 (±0.5) | 45.4 (±6.9) | 23.6 |
| 108 | s-Butyl | 3-CF₃-phenethyl | 3.4 (±0.7) | 35.9 (±12.1) | 10.5 |
| 109 | Cyclohexylmethyl | 3-Cl-phenethyl | 1.5 (±0.7) | 44.6 (±5.5) | 30.5 |
| 110 | Cyclohexylmethyl | 4-Cl-phenethyl | 1.7 (±0.8) | 46.8 (±1.7) | 27.3 |
| 111 | Cyclohexylmethyl | 3-CF₃-phenethyl | 0.9 (±0.2) | 20.4 (±3.3) | 22.1 |
| 9 | (±)-2-endo-Norbonyl | 3-Cl-phenethyl | 0.8 (±0.1) | 20.1 (±5.0) | 25.1 |
| 10 | (±)-2-endo-Norbonyl | 4-Cl-phenethyl | 0.6 (±0.1) | 13.5 (±3.1) | 22.5 |
| 112 | (±)-2-exo-Norbonyl | 3-Cl-phenethyl | 1.9 (±0.1) | 6.3 (±1.7) | 3.3 |
| 113 | (±)-2-exo-Norbonyl | 4-Cl-phenethyl | 2.8 (±0.02) | 10.9 (±2.5) | 3.9 |
| 114 | 1-Adamantyl | 4-Cl-phenethyl | 3.2 (±1.4) | 2.6 (±1.1) | 0.8 |
| 115 | 1-Adamantyl | 3-Cl-phenethyl | 2.6 (±1) | 1.9 (±0.6) | 0.7 |
| 116 | 2-Adamantyl | 4-Cl-phenethyl | 2.5 (±0.9) | 40.4 (±29.7) | 18.3 |
| 117 | 2-Adamantyl | 3-Cl-phenethyl | 1.6 (±0.6) | 3.1 (±1.6) | 2.0 |

TABLE 4

IC$_{50}$ values and selectivity of PYT analogues after lead modification

| Set | Name | Structure | IC$_{50}$ (μM)$^{a,b}$ Cav1.3 | Cav1.2 | Selectivity$^c$ |
|---|---|---|---|---|---|
| 1st | 1 | 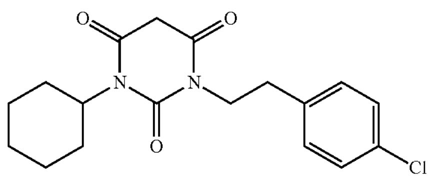 [SMILES: O=C1CC(=O)N(C2CCCCC2)C(=O)N1CCc1ccc(Cl)cc1] | 1.1 | 38.8 | 35 |
| | 2 | | 1.3 | 43.8 | 34 |
| | 3 | | 1.4 | 53.1 | 38 |
| 2nd | 4 | 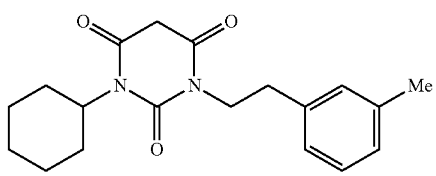 [SMILES: Cc1cccc(CCN2C(=O)CC(=O)N(C3CCCCC3)C2=O)c1] | 2.2 | 77.1 | 35 |
| | 5 | | 1.3 | 45.8 | 34 |
| | 6 | | 1.3 | 25.8 | 20 |
| 3rd | 7 | 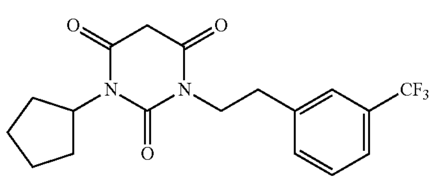 [SMILES: O=C1CC(=O)N(C2CCCC2)C(=O)N1CCc1cccc(C(F)(F)F)c1] | 1.1 | 326 | 305 |
| | 8 | | 1.7 | 1730 | 1008 |

TABLE 4-continued

IC$_{50}$ values and selectivity of PYT analogues after lead modification

| Set | Name | Structure | IC$_{50}$ (μM)[a,b] Cav1.3 | Cav1.2 | Selectivity[c] |
|---|---|---|---|---|---|
| 9 | | 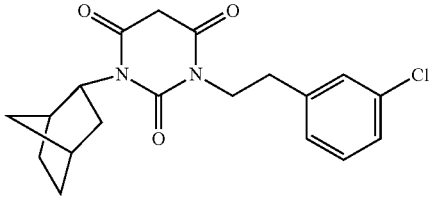 (±)-endo | 0.8 | 20.1 | 25 |
| 10 | | 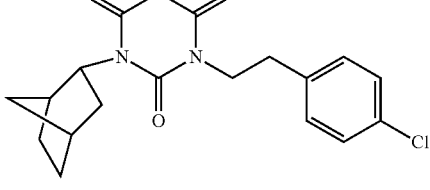 (±)-endo | 0.6 | 13.5 | 23 |

[a] The IC$_{50}$ were determined with dose-response curves with 12 concentration points (0.1 nM~100 μM) in duplicate to determine an IC$_{50}$ value and an associated standard deviation.
[b] IC$_{50}$ and associated standard deviation values of all library members are described in Supporting Information Tables A1~A3.
[c] The selectivity of antagonism for Cav1.3 relative to Cav1.2 channels was determined by the inverse of the ratio of the IC$_{50}$ value with Cav1.2 channels to that with Cav1.3 channels.

Pharmacophoric Model.

Figure 7:
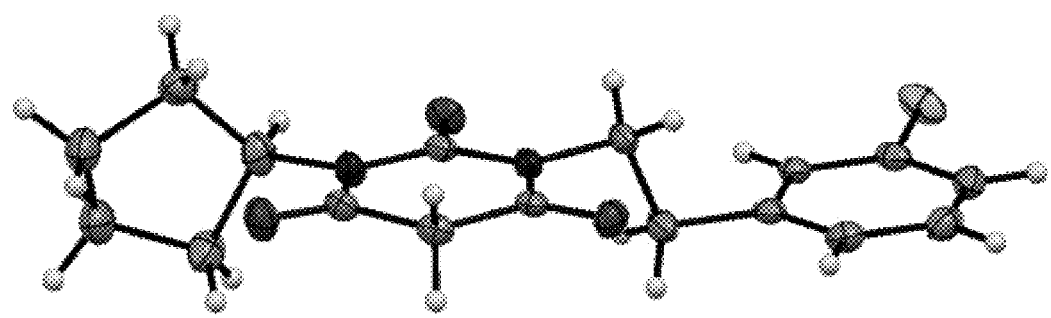
FIG. 7 shows an image of an X-ray crystal structure of compound 8.

X-ray crystallography analysis of 8 shows that the PYT ring is oriented perpendicular to the plane of the cycloalkyl ring (SEE FIG. 7). Since the most selective PYTs have an N-substituted cycloalkyl group, it is reasonable to assume that the Cav1.3 channel can accommodate a PYT ring twisted relative to the plane of the N-cycloalkyl group, but the Cav1.2 channel cannot.

Three general pharmacophores can be drawn after analyzing all of the trends. First, the most selective compounds for Cav1.3 channels have a cyclohexyl or cyclopentyl substituent (R$_1$) on the PYT skeleton, implying that a perpendicularly arranged 5 or 6-membered alkyl ring is needed for selective antagonism of the Cav1.3 channels. Second, a meta-substituted phenethyl moiety (R$_2$) improves selectivity for the Cav1.3 channels. Third, Cav1.3 channels respond to a variety of bulky structures at the cycloalkyl binding site. However, substituents with exceptional steric demand bind non-selectively.

Bioactivity Confirmation Using Whole-Cell Patch Clamp.

Figure 8:
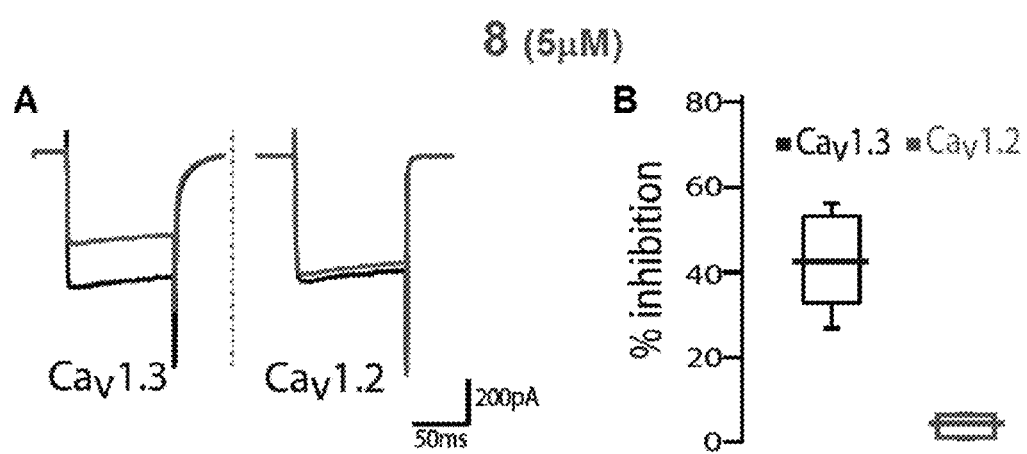
FIG. 8 shows (A) whole-cell voltage-clamp recordings of Cav1.3 and Cav1.2 channels with compound 8 (5 μM). (B) Group data for the action of select PYTs on Cav1.3 or Cav1.2 LTCCs.
Figure 9:
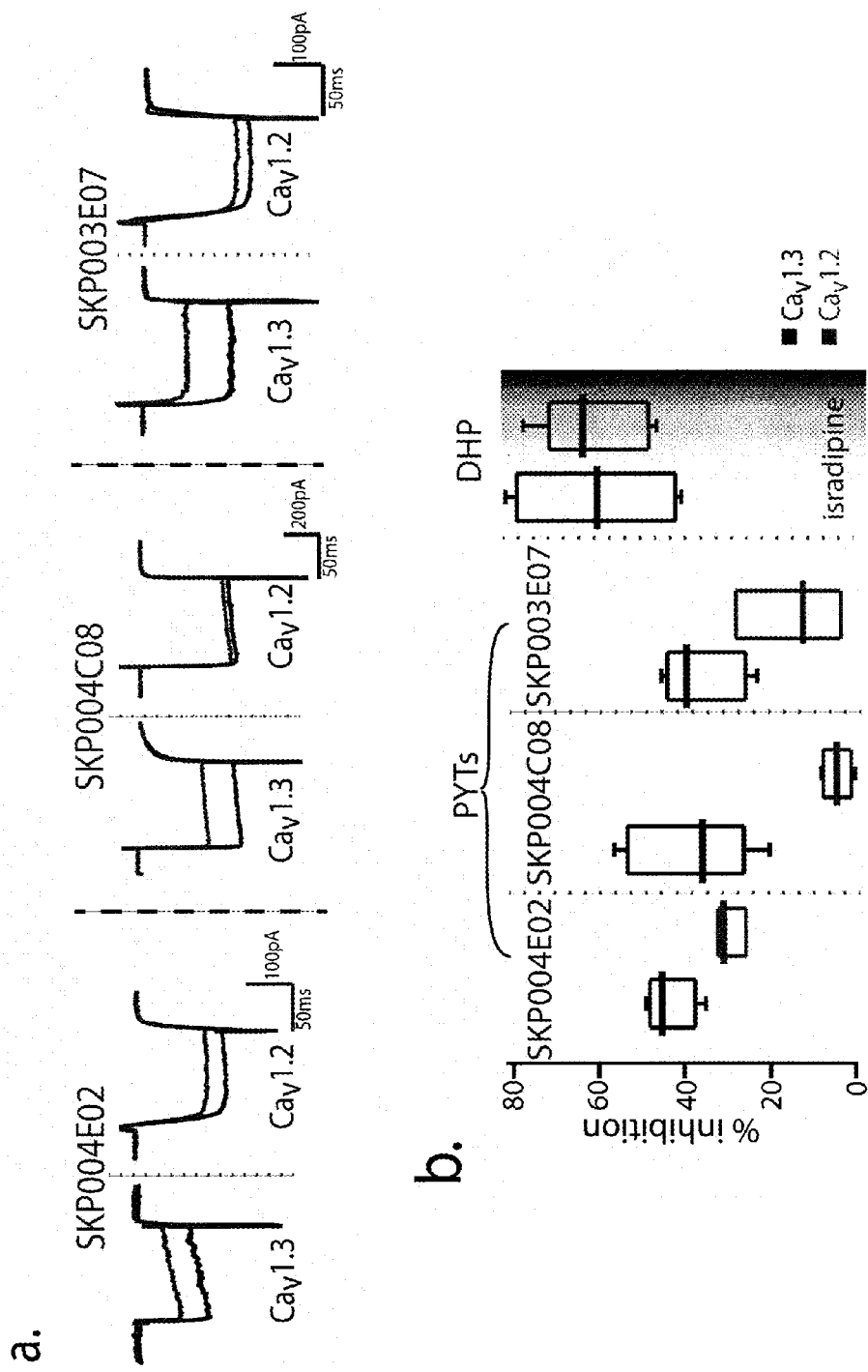
FIG. 9 shows (A) whole-cell voltage-clamp recordings of Cav1.3 and Cav1.2 channels with compounds: SKP004E02 (3 μM), SKP004C08 (5 μM), and SKP003E07 (5 μM). Example currents were resolved from a voltage step from −70 mV to 0 mV from either Cav1.3 or Cav1.2 LTCCs (B) Population data set of SKP004E02, SKP004C08, and SKP003E07 on both Cav1.3 and Cav1.2 LTCCs.
Figure 10:
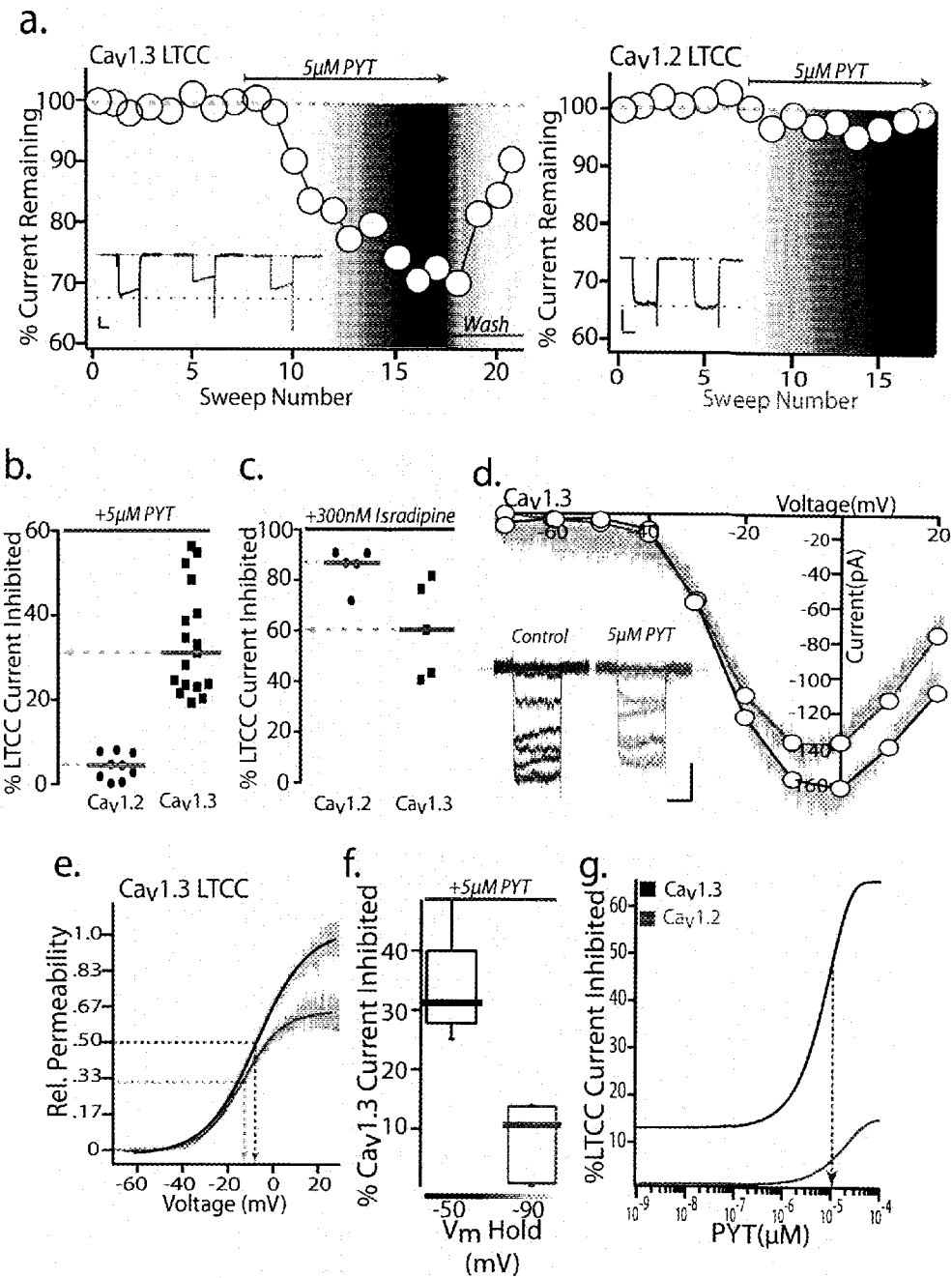
FIG. 10 a. shows Cav1.3 and Cav1.2 LTCCs peak currents with application of 5 μM PYT (SKP004-C08). b. Population data of the effect of 5 μM PYT and c. Isradipine (300 nM). d. I-V plot of the Cav1.3 LTCC stable currents evoked from −70 mV to +30 mV voltage step, from a holding potential of −80 mV. The solid lines are currents evoked from a slow voltage ramp. Inlet, responses from steady voltage steps. e. GHK constant equation fit to currents evoked from ramp voltage ramps, black (control), red (5 μM PYT). f. PYT effect on Cav1.3 current from different holding potentials. g. PYT dose-response curve of Cav1.3 and Cav1.2 LTCCs.
Figure 11:
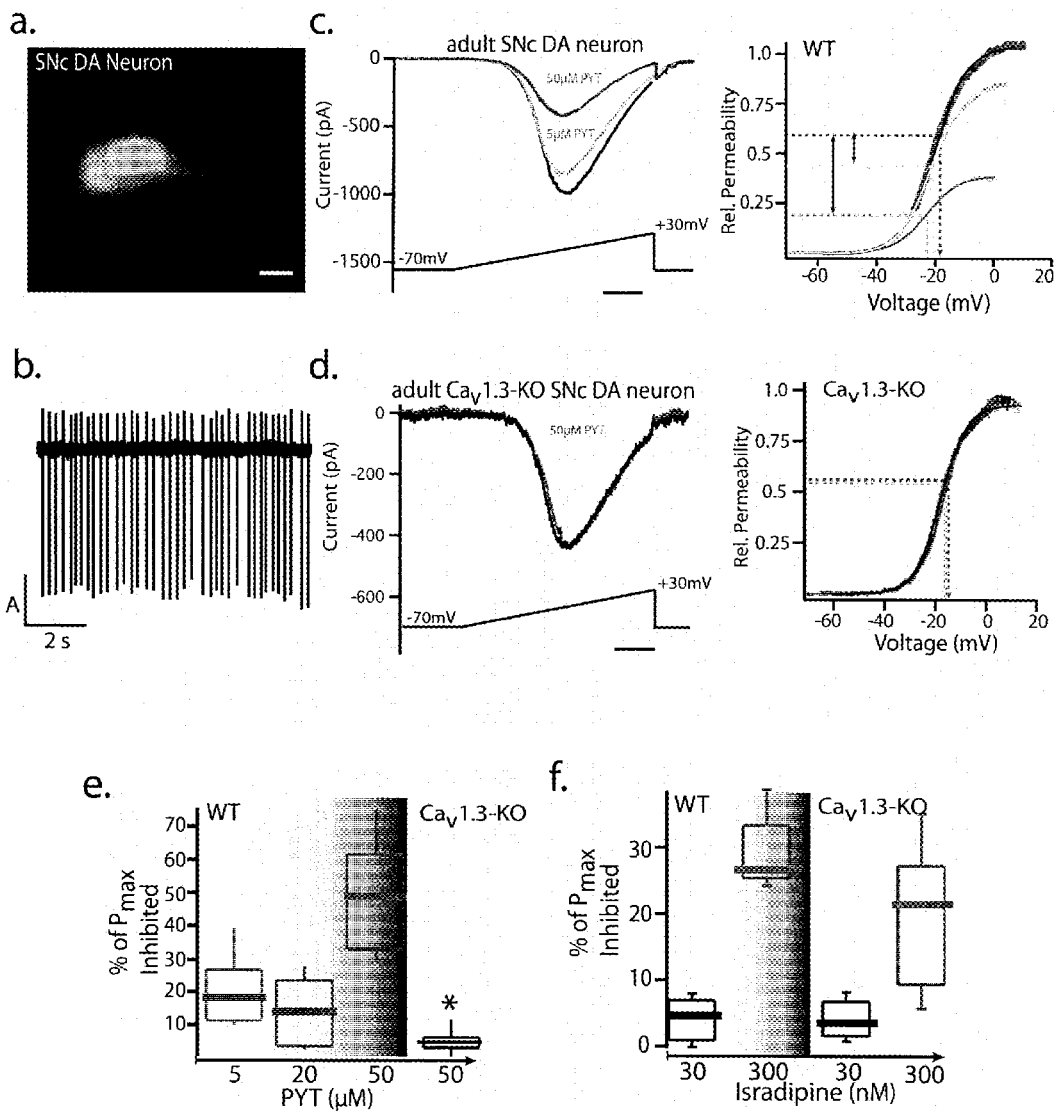
FIG. 11 a. shows fluorescent detection of SNc DA neurons. b. SNc DA neuron firing in cell-attached mode. c. Current response to voltage ramp from WT-adult TH+ mice. d. Current response to voltage ramp from Cav1.3-KO D2-eGFP. e. Population data with PYT application. f. Population data with isradipine application.
Figure 12:
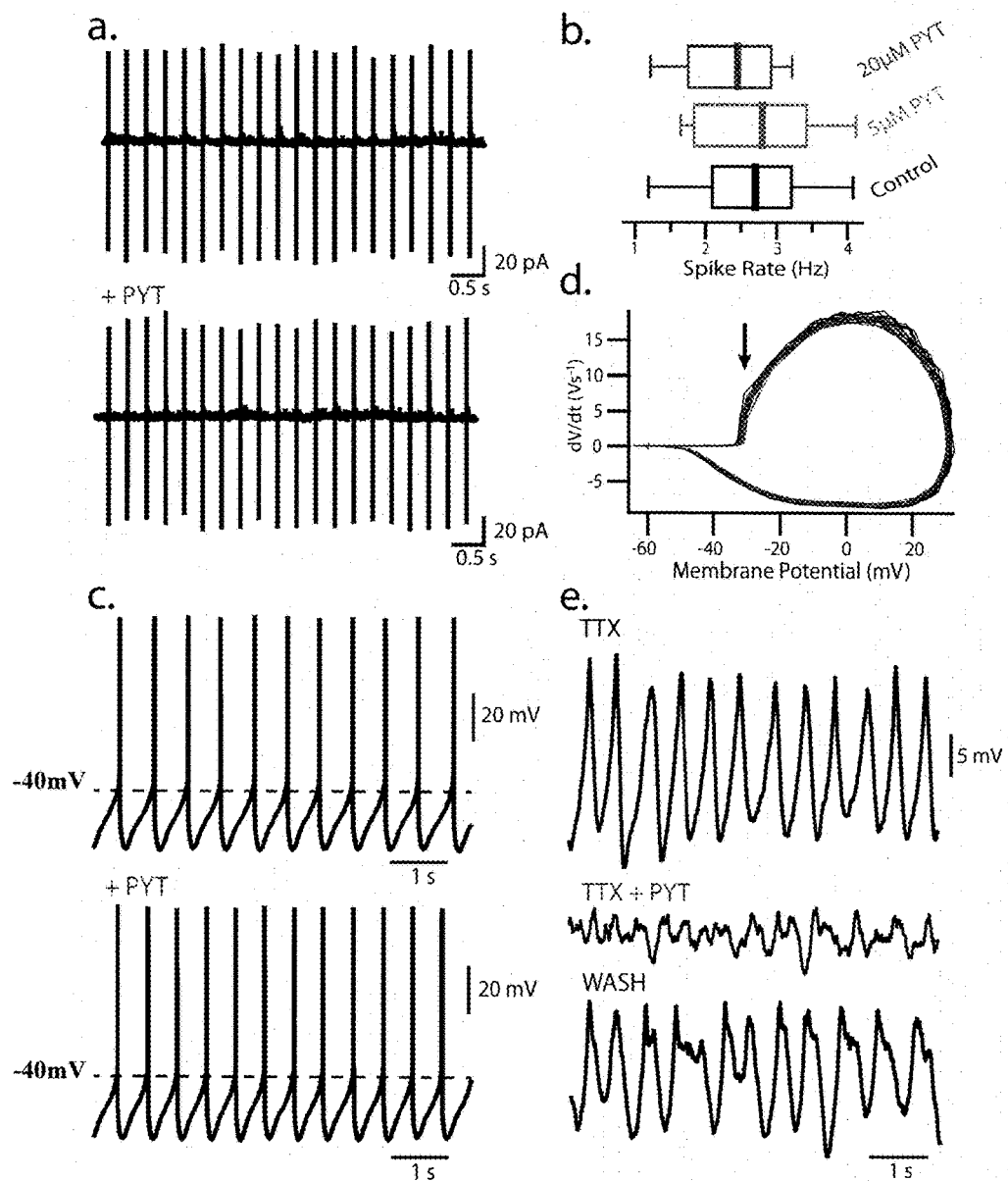
FIG. 12 shows: (A) cell-attached recording of SNc neuron in a brain slice experiment shows autonomous pacemaking activity that application of PYT does not interrupt. (B) Both 5 and 20 uM PYT does not change basal firing rate in SNc neurons. (C) whole-cell current clamp recording shows no significant change in action potential waveform with the application of PYT and (D) no change in action potential threshold. (E) Application of tetrodotoxin reveals underlying, calcium-dependent subthreshold oscillations that are reversibly blocked by PYT.
Figure 13:
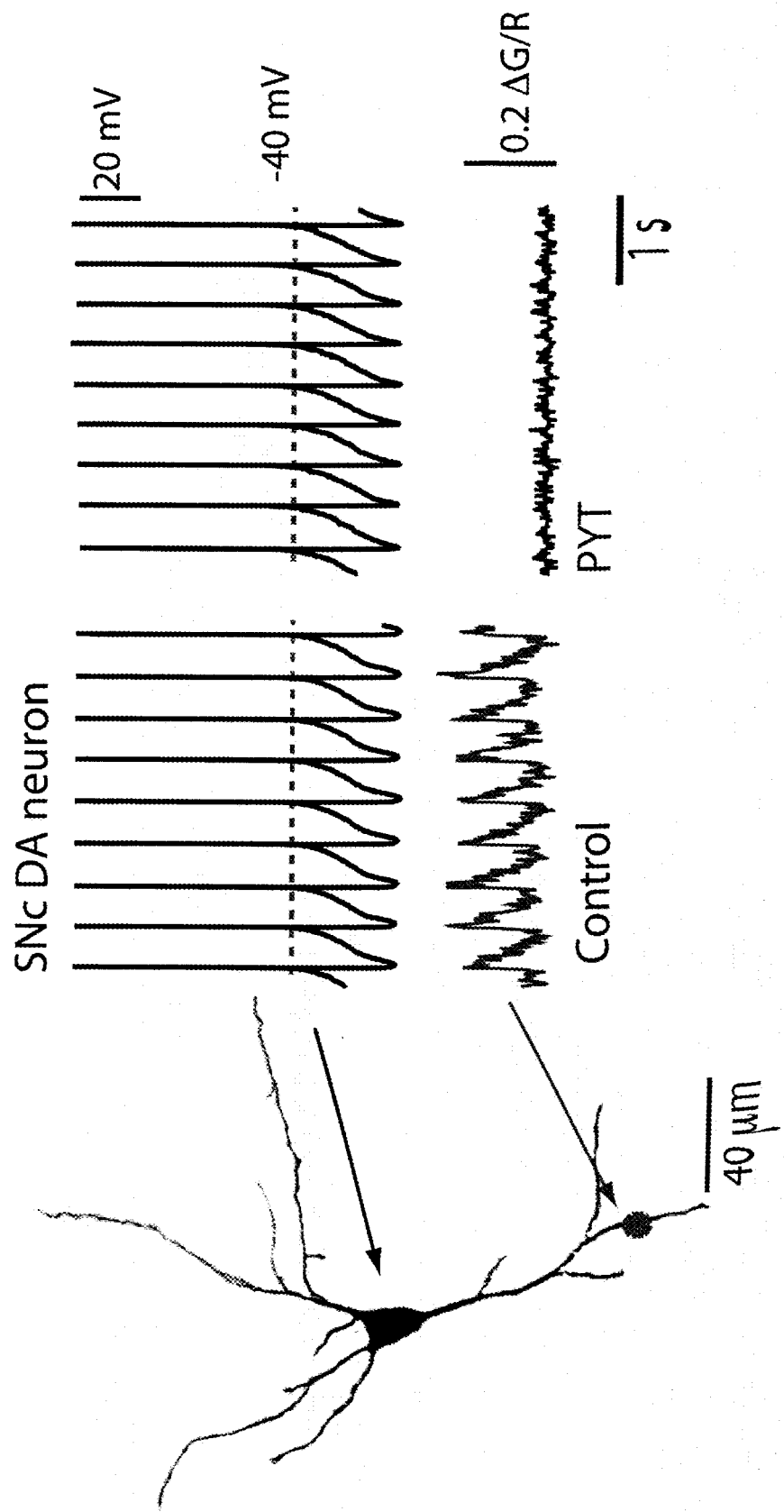
FIG. 13 shows two-photon calcium imaging of distal dendritic calcium oscillations in SNc neurons are blocked with application of PYT with no accompanying change in firing rate.

Because IC$_{50}$ values depend strongly on assay conditions, the inhibitory activity of compound 8 (SKP004C08) was confirmed at Cav1.3 and Cav1.2 channels in HEK293 cells by whole-cell voltage-clamp electrophysiological recordings (FIG. 8).

Figure 5:
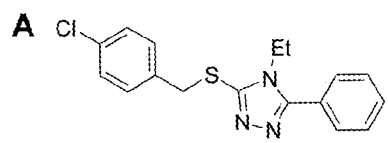
FIG. 5 shows structures of HTS hit compounds thiotriazole and PYT.
Figure 5:
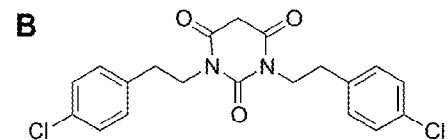

Whole-cell voltage-clamp recordings (FIG. 8A) were made in the absence (black, top) or presence (red, top) of compound 8 (SKP004C08) (5 μM). Superfusion of selected PYT blocks evoked barium currents in both LTCC cell lines in keeping with the data from our initial screen (FIG. 5B). Compound 8 at 5 μM concentration exhibits 43.8±11% and 3.8±2.9% inhibition of Cav1.3 and Cav1.2 channels, respectively. The inhibition ratio for 8 at 5 μM is roughly 12-fold, similar to the results of the FLIPR assay (11-fold at 5.5 These results confirm that PYT is a viable selective antagonist scaffold, and (SKP004C08) is a very selective analogue.

General Procedure for High-Throughput Screening.

Cav1.3 or Cav1.2 channel inhibition was determined using Screen Quest Fluo-8 NW Calcium Assay Kit (ABD Bioquest Inc, Sunnyvale, Calif., USA) on a FLIPR tetra (Molecular Devices LLC, Sunnyvale, Calif., USA) as follows: HEK293 cells (4×10$^4$ cells/well) expressing either Cav1.2 or Cav1.3 L-type Ca$^{2+}$ channels were cultured in DMEM with 10% FBS for 4 days on tissue culture-treated, 384 well, clear bottom black plates (Greiner Bio-One North America, Inc., Monroe, N.C., USA). The assay plates were coated with BD Matrigel matrix to improve cell adherence. Dilution series of lead compounds were generated in separate 384 well plates using an Echo550 acoustic liquid transfer system (Labcyte Inc, Sunnyvale, Calif., USA). Fluo-8 reagent was prepared in HBSS(+) solution (Hanks Buffered Saline Solution with 20 mM Hepes and 5 mM additional CaCl added, pH 7.4). Then 100 uL of the Fluo-8 reagent was added to the compound dilution series and controls and well mixed by pipetting using a Biomek FX liquid handler (Beckman Coulter Inc, Brea, Calif., USA). The media was then removed from the cells and 45 uL of the compound/Fluo-8 mixture was transferred to assay plates of each cell line using the Biomek FX. The treated cells were incubated at 37° C. for 45 min and then removed from the incubator and placed at room temperature for an additional 30 min. The plates were placed in the FLIPR tetra, which was programmed to measure the fluorescence intensity before, during, and for 2 min after adding 25 uL of KCl solution (450 mM KCl in HBSS(+) solution, pH 7.4). FLIPR tetra data acquisition parameters were as follows: excitation wavelength 470-495 nm, emission wavelength 515-575 nm, gain 80, exposure 0.4 s, excitation intensity 80. Each assay plate included at least 32 reference wells containing no compounds from which the in-plate assay readout dynamic range was determined, which was used as 100% readout signal to calculate the percentage of inhibition of a compound well.

General Procedure for Whole-cell Patch Clamp.

HEK-293 cells were stably transfected with rat Cav1.3 ($\alpha_1$D) or rabbit Cav1.2 ($\alpha_1$C), Cavβ$_3$, and Cavα$_2$δ-1 and were cultured as previously reported (Chan et al. (2007) *Nature* 447:1081-1086.; herein incorporated by reference in its entirety). After 24-48 h of incubation at 37° C., cells underwent whole-cell patch-clamp electrophysiology. The external solution contained the following (in mM): 140 NaCl, 1 MgCl$_2$, 10 BaCl$_2$, 10 HEPES, 10 dextrose, 10 sucrose, and 20 CsCl at pH 7.4 and an osmolarity of ~320 mOSml$^{-1}$. The test compound stock solutions in DMSO (10 mM or just DMSO) were diluted with the external solution to the desired concentration ($10^{-9}$ to $10^{-6}$M), which was perfused (2 mL/min) into the bath while measuring the evoked barium currents. For experiments where dose-response curves were obtained, local perfusion of the desired concentration was employed. Barium currents were measured from whole-cell voltage patch-clamp recordings using a Pulse 8.4 software data acquisition system (HEKA, Germany). Signals were low-pass filtered at 1 kHz, digitized (sampled) at 10 kHz, and were amplified with an Axopatch 200B patch-clamp amplifier (Axon Instruments). Barium currents were evoked by a voltage step and/or ramp from varying holding potentials of −70 mV at room temperature (22-25° C.), unless otherwise noted. Patch pipettes were pulled from thick-walled borosilicate glass and maintained at a resistance of approximately 3-5 mΩ. Internal pipette solutions contained the following (in mM): 180 NMG (N-methyl-D-glucosamine), 40 HEPES, 4 MgCl$_2$, 12 phosphocreatine, 0.1 leupeptin, 2 Na$_2$ATP, 0.5 Na$_3$GTP, 5 BAPTA, pH 7.2-7.3, and an osmolarity of ~300 mOSml$^{-1}$. Electrophysiological signals were analyzed using CLAMPFIT 8.2 (Axon Instruments) and IGORPRO6 software.

General for Pyrimidinetrione Synthesis.

Reagents were purchased from Sigma-Aldrich, Alfa-Aesar, and TCI America and used without further purification. Solvents were purified by passage through a solvent column composed of activated alumina and a supported copper redox catalyst. Reactions were monitored by thin-layer chromatography (TLC) carried out on EMD silica gel plates (2.5 cm×7.5 cm, 250 µm thick, 60 F254), visualized by using UV (254 nm) and ninhydrin stain. Flash chromatography was performed using Sorbent silica gel (230-400 mesh, grade 60). $^1$H NMR and $^{13}$C NMR spectra were recorded in the indicated solvent with tetramethylsilane (TMS) or the residual solvent peak as the internal standard on a Bruker Avance-III (500 MHz and 125 MHz for $^1$H and $^{13}$C, respectively) spectrometer. Chemical shifts are given in ppm (δ) relative to the internal standard, and coupling constants (J) are in Hertz (Hz). Abbreviations for the multiplicities of the signals are as follows: s (singlet), d (doublet), t (triplet), q (quartet), m (multiplet), and br s (broad singlet). MS was performed on a system consisting of an electrospray ionization (ESI) source in a Thermo Finnigan LCQ mass spectrometer. High resolution mass spectra were obtained using an Agilent 6210 LC-TOF spectrometer.

Synthetic Procedure.

To an isocyanate (1 mmol) in dry dichloromethane (10 mL) was added an amine (1 mmol), and the mixture was stirred at room temperature for 3-5 h. After dilution with dry dichloromethane (50 mL), malonyl chloride (1.1 mmol) was added dropwise under vigorous stirring at room temperature for 5 min. The resulting pale yellow solution was stirred for an additional 1 h and concentrated at reduced pressure to a small volume. The resultant reaction mixture was purified by flash chromatography on 50 g of silica gel in a column (20 mm ID) using 20-33% ethyl acetate in hexanes to give analytically pure compound (20~90% yield).

N-(4-chlorophenethyl)-N'-cyclohexyl-pyrimidine-2, 4,6-(1H,3H,5H)-trione (1)

White powder; mp 146-148° C.; $^1$H NMR (CDCl$_3$, 500 MHz): δ 7.27 (d, 2H, J=8.4 Hz), 7.17 (d, 2H, J=8.4 Hz), 4.59 (m, 1H), 4.06 (m, 2H), 3.61 (s, 2H), 2.86 (m, 2H), 2.21 (m, 2H), 1.84 (m, 2H), 1.68 (m, 1H), 1.59 (m, 2H), 1.35 (m, 2H), 1.22 (m, 1H) ppm; $^{13}$C NMR (CDCl$_3$, 125 MHz): δ 164.5, 151.1, 136.3, 132.6, 130.3, 128.7, 55.4, 42.8, 40.2, 33.3, 29.0, 26.3, 25.1 ppm; HRMS (ESI) calculated for C$_{18}$H$_{21}$ClN$_2$O$_3$[M-H]$^-$: 347.1168; found, 347.1166.

N-cyclopenyl-N'-(4-phenylbutyl)-pyrimidine-2,4,6-(1H,3H,5H)-trione (2)

White powder; mp 85-87° C.; $^1$H NMR (CDCl$_3$, 500 MHz): δ 7.28-7.16 (m, 5H), 5.13 (m, 1H), 3.87 (m, 2H), 3.59 (s, 2H), 2.64 (m, 2H), 1.95 (m, 4H), 1.83 (m, 2H), 1.64 (m, 4H), 1.59 (m, 2H) ppm; $^{13}$C NMR (CDCl$_3$, 125 MHz): δ 164.9, 164.6, 151.0, 142.0, 128.4, 128.3, 125.8, 54.2, 41.7, 40.1, 35.4, 28.7, 28.6, 27.6, 25.6 ppm; HRMS (ESI) calculated for C$_{19}$H$_{24}$N$_2$O$_3$[M-H]$^-$: 327.1714; found, 327.1719.

N-(3-chlorophenethyl)-N'-cyclohexyl-pyrimidine-2, 4,6-(1H,3H,5H)-trione (3)

White powder; mp 153-154° C.; $^1$H NMR (CDCl$_3$, 500 MHz): δ 7.27-7.12 (m, 4H), 4.60 (m, 1H), 4.06 (m, 2H), 3.61 (s, 2H), 2.87 (m, 2H), 2.22 (m, 2H), 1.84 (m, 2H), 1.60 (m, 2H), 1.34 (m, 2H), 1.26 (m, 2H) ppm; $^{13}$C NMR (CDCl$_3$, 125 MHz): δ 164.7, 164.5, 151.1, 139.8, 134.3, 129.8, 129.1, 127.1, 126.9, 55.4, 42.6, 40.2, 33.6, 29.0, 26.3, 25.1 ppm; HRMS (ESI) calculated for C$_{18}$H$_{21}$ClN$_2$O$_3$[M-H]$^-$: 347.1168; found, 347.1171.

N-cyclohexyl-N'-(3-methylphenethyl)-pyrimidine-2, 4,6-(1H,3H,5H)-trione (4)

White powder; mp 182-183° C.; $^1$H NMR (CDCl$_3$, 500 MHz): δ 7.21-7.06 (m, 4H), 4.62 (m, 1H), 4.08 (m, 2H), 3.62 (s, 2H), 2.87 (m, 2H), 2.35 (s, 3H), 2.25 (m, 2H), 1.86 (m, 2H), 1.67-1.55 (m, 3H), 1.40-1.19 (m, 3H) ppm; $^{13}$C NMR (CDCl$_3$, 125 MHz): δ 164.9, 164.6, 151.2, 138.2, 137.8, 129.8, 128.5, 127.4, 126.0, 55.4, 43.1, 40.3, 33.9, 29.1, 26.3, 25.1, 21.4 ppm; HRMS (ESI) calculated for C$_{19}$H$_{24}$N$_2$O$_3$ [M-H]$^-$: 327.1714; found, 327.1719.

N-(3-bromophenethyl)-N'-cyclohexyl-pyrimidine-2, 4,6-(1H,3H,5H)-trione (5)

White powder; mp 154-155° C.; $^1$H NMR (CDCl$_3$, 500 MHz): δ 7.32 (m, 2H), 7.11 (m, 2H), 4.53 (m, 1H), 3.99 (m, 2H), 3.54 (s, 2H), 2.80 (m, 2H), 2.16 (m, 2H), 1.77 (m, 2H), 1.61-1.53 (m, 3H), 1.31-1.11 (m, 3H) ppm; $^{13}$C NMR (CDCl$_3$, 125 MHz): δ 164.7, 164.6, 151.1, 140.1, 132.0, 130.2, 129.9, 127.6, 122.6, 55.4, 42.7, 40.2, 33.6, 29.1, 26.3, 25.14 ppm; HRMS (ESI) calculated for C$_{18}$H$_{21}$BrN$_2$O$_3$[M-H]$^-$: 391.0663; found, 391.0665.

N-cyclohexyl-N'-(3-thrifluoromethylphenethyl)-pyrimidine-2,4,6-(1H,3H,5H)-trione (6)

White powder; mp 105-107° C.; $^1$H NMR (CDCl$_3$, 500 MHz): δ 7.46 (m, 4H), 4.60 (m, 1H), 4.10 (m, 2H), 3.62 (s, 2H), 2.97 (m, 2H), 2.22 (m, 2H), 1.83 (m, 2H), 1.69-1.59 (m, 3H), 1.39-1.11 (m, 3H) ppm; $^{13}$C NMR (CDCl$_3$, 125 MHz): δ 164.7, 164.6, 151.1, 138.8, 132.4, 130.8 (q, J=31.9 Hz), 129.1, 125.7 (q, J=3.6 Hz), 124.1 (q, J=271.1 Hz), 123.6 (q, J=3.7 Hz), 55.4, 42.6, 40.2, 33.8, 29.0, 26.3, 25.1 ppm; HRMS (ESI) calculated for C$_{19}$H$_{21}$F$_3$N$_2$O$_3$[M-H]$^-$: 381.1432; found, 381.1439.

N-cyclopentyl-N'-(3-thrifluoromethylphenethyl)-pyrimidine-2,4,6-(1H,3H,5H)-trione (7)

White powder; mp 97-98° C.; $^1$H NMR (CDCl$_3$, 500 MHz): δ 7.50-7.43 (m, 4H), 5.15 (m, 1H), 4.12 (m, 2H), 3.64 (s, 2H), 2.99 (m, 2H), 1.94 (m, 4H), 1.85 (m, 2H), 1.60 (m, 2H) ppm; $^{13}$C NMR (CDCl$_3$, 125 MHz): δ 164.7, 164.5, 150.9, 138.8, 132.4, 130.9 (q, J=32.1 Hz), 129.1, 125.7 (q, J=3.5 Hz), 124.1 (q, J=271.2 Hz), 123.6 (q, J=3.6 Hz), 54.3, 42.6, 40.1, 33.8, 28.7, 25.6 ppm; HRMS (ESI) calculated for C$_{18}$H$_{19}$F$_3$N$_2$O$_3$[M-H]$^-$: 367.1275; found, 367.1272.

N-(3-chlorophenethyl)-N'-cyclopentyl-pyrimidine-2,4,6-(1H,3H,5H)-trione (8)

White powder; mp 131-132° C.; $^1$H NMR (CDCl$_3$, 500 MHz): δ 7.23-7.13 (m, 4H), 5.14 (m, 1H), 4.07 (m, 2H), 3.63 (s, 2H), 2.88 (m, 2H), 1.94 (m, 4H), 1.84 (m, 2H), 1.59 (m, 2H) ppm; $^{13}$C NMR (CDCl$_3$, 125 MHz): δ 164.8, 164.5, 150.9, 139.9, 134.3, 129.9, 129.1, 127.2, 126.9, 54.3, 42.6, 40.1, 33.7, 28.7, 25.6 ppm; HRMS (ESI) calculated for C$_{17}$H$_{19}$ClN$_2$O$_3$[M-H]$^-$: 333.1011; found, 333.1019.

N-(3-chlorophenethyl)-N'-(+)-endo-norbornyl-pyrimidine-2,4,6-(1H,3H,5H)-trione (9)

White powder, mp 155-157° C.; $^1$H NMR (CDCl$_3$, 500 MHz): δ 7.28-7.15 (m, 4H), 4.63 (m, 1H), 4.09 (m, 2H), 3.65 (dd, 2H, J=21.1 Hz, J=30.4 Hz), 2.89 (m, 2H), 2.61 (m, 1H), 2.37 (m, 1H), 2.20 (m, 1H), 1.75-1.67 (m, 2H), 1.54 (m, 1H), 1.48-1.30 (m, 4H) ppm; $^{13}$C NMR (CDCl$_3$, 125 MHz): δ 165.9, 164.5, 152.2, 139.9, 134.3, 129.8, 129.1, 127.2, 127.0, 59.7, 42.8, 42.1, 40.9, 37.8, 37.6, 33.7, 29.5, 28.8, 23.9 ppm; HRMS (ESI) calculated for C$_{19}$H$_{21}$ClN$_2$O$_3$[M-H]$^-$: 359.1163; found, 359.1169.

N-(4-chlorophenethyl)-N'-(+)-endo-norbornyl-pyrimidine-2,4,6-(1H,3H,5H)-trione (10)

White powder, mp 121-123° C.; $^1$H NMR (CDCl$_3$, 500 MHz): δ 7.28 (d, 2H, J=8.4 Hz), 7.19 (d, 2H, J=8.4 Hz), 4.60 (m, 1H), 4.09 (m, 2H), 3.64 (dd, 2H, J=21.2 Hz, J=31.0 Hz), 2.88 (m, 2H), 2.59 (m, 1H), 2.36 (m, 1H), 2.20 (m, 1H), 1.76-1.65 (m, 2H), 1.54 (m, 1H), 1.47-1.31 (m, 4H) ppm; $^{13}$C NMR (CDCl$_3$, 125 MHz): δ 165.9, 164.6, 152.2, 136.3, 132.6, 130.4, 128.7, 59.7, 42.9, 42.1, 40.9, 37.7, 37.6, 33.4, 29.5, 28.8, 23.8 ppm; HRMS (ESI) calculated for C$_{19}$H$_{21}$ClN$_2$O$_3$[M-H]$^-$: 359.1168; found, 359.1169.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

What is claimed is:

1. A method of selectively inhibiting a Cav1.3-calcium ion channel, comprising contacting said Cav1.3-calcium ion channel with a compound of the formula:

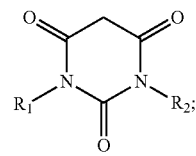

wherein R1 is a norbornyl group, and R2 is a para-substituted phenethyl group, wherein the compound is a selective Cav1.3-calcium ion channel inhibitor.

2. The method of claim 1, wherein said para-substituted phenethyl group comprises a single non-hydrogen substituent at the para-position selected from the group consisting of: F, Cl, Br, CF$_3$, CO$_2$H, CN, NO$_2$, MeO, and Me.

3. The method of claim 1, wherein said compound has the formula:

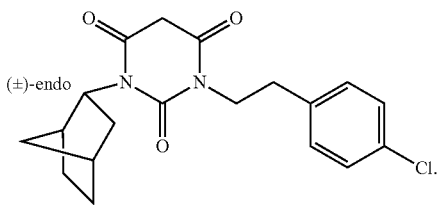 [SMILES: O=C1CC(=O)N(C2CC3CCC2C3)C(=O)N1CCc1ccc(Cl)cc1]

4. The method of claim 1, wherein said compound has the formula:

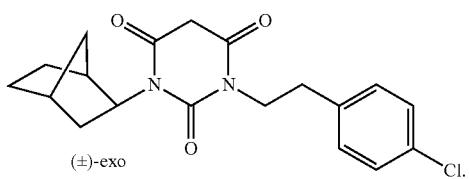 [SMILES: O=C1CC(=O)N(C2CC3CCC2C3)C(=O)N1CCc1ccc(Cl)cc1]

5. A method of treating a neurodegenerative disorder comprising administering to a subject a Cav1.3-selective calcium ion channel antagonist of the formula:

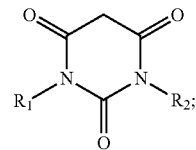

wherein R1 is a norbornyl group, and R2 is a para-substituted phenethyl group, wherein the compound is a selective Cav1.3-calcium ion channel inhibitor, and wherein treating is not preventing.

6. The method of claim 5, wherein said neurodegenerative disorder comprises Parkinson's disease.

7. The method of claim 5, wherein said neurodegenerative disorder comprises Alzheimer's disease.

8. The method of claim 5, wherein said subject suffers from a neurodegenerative disorder.

9. The method of claim 5, wherein said subject has one or more risk factors for a neurodegenerative disorder.

10. The method of claim 9, wherein said risk factors for a neurodegenerative disorder comprise: increased age, genetic polymorphisms linked to neurodegenerative disorders, environmental factors, gender, education, endocrine conditions, oxidative stress, inflammation, stroke, hypertension, diabetes, smoking, head trauma, depression, infection, tumors, vitamin deficiencies, immune and metabolic conditions, and chemical exposure.

11. The method of claim 1, wherein the compound is administered to a subject suffering from a neurodegenerative disorder.

12. The method of claim 11, wherein said neurodegenerative disorder comprises Parkinson's disease.

13. The method of claim 11, wherein said neurodegenerative disorder comprises Alzheimer's disease.

14. The method of claim 11, wherein said compound is administered to treat said neurodegenerative disorder.

15. The method of claim 11, wherein said subject has one or more risk factors for a neurodegenerative disorder.

16. The method of claim 15, wherein said risk factors for a neurodegenerative disorder comprise: increased age, genetic polymorphisms linked to neurodegenerative disorders, environmental factors, gender, education, endocrine conditions, oxidative stress, inflammation, stroke, hypertension, diabetes, smoking, head trauma, depression, infection, tumors, vitamin deficiencies, immune and metabolic conditions, and chemical exposure.

* * * * *